(12) United States Patent
Hakki et al.

(10) Patent No.: US 10,821,281 B1
(45) Date of Patent: Nov. 3, 2020

(54) IMPLANTABLE PACING AND DEFIBRILLATION SYSTEM WITH ILLUMINATED GENERATORS

(71) Applicants: A-Hamid Hakki, Dunedin, FL (US); A-Hadi Hakki, Largo, FL (US)

(72) Inventors: A-Hamid Hakki, Dunedin, FL (US); A-Hadi Hakki, Largo, FL (US)

( * ) Notice: Subject to any disclaimer, the term of this patent is extended or adjusted under 35 U.S.C. 154(b) by 0 days.

(21) Appl. No.: 16/550,561

(22) Filed: Aug. 26, 2019

Related U.S. Application Data

(63) Continuation-in-part of application No. 15/691,924, filed on Aug. 31, 2017, now Pat. No. 10,500,394, which is a continuation-in-part of application No. 15/042,301, filed on Feb. 12, 2016, now Pat. No. 9,775,991, which is a continuation-in-part of application No. 13/649,792, filed on Oct. 11, 2012, now Pat. No. 9,289,593.

(60) Provisional application No. 61/545,913, filed on Oct. 11, 2011.

(51) Int. Cl.
| | |
|---|---|
| *A61N 1/05* | (2006.01) |
| *A61N 7/00* | (2006.01) |
| *A61N 1/362* | (2006.01) |

(52) U.S. Cl.
CPC ............. *A61N 1/057* (2013.01); *A61N 1/362* (2013.01); *A61N 7/00* (2013.01)

(58) Field of Classification Search
CPC ....... A61N 1/3756; A61N 1/362; A61N 1/057
See application file for complete search history.

(56) References Cited

U.S. PATENT DOCUMENTS

| | | | | |
|---|---|---|---|---|
| 5,638,832 A | * | 6/1997 | Singer | A01K 11/006 128/899 |
| 2016/0120469 A1 | * | 5/2016 | Freeman | A61B 5/14539 600/479 |

* cited by examiner

*Primary Examiner* — Alyssa M Alter
(74) *Attorney, Agent, or Firm* — Rosenberg, Klein & Lee

(57) ABSTRACT

A pacemaker defibrillator system implantable in the intercostal space of a mammalian patient is configured with sensors to sense electrical, mechanical and blood flow activity of the heart from the base to the apex, and the patient position, and to generate corresponding signals responsive to the sensed cardiac situation, as well as to provide instantaneous display of the cardiac situation and the system operational situation using an LCD and multicolor LEDs generating signals which can be seen through the skin of the patient. The system includes at least two flexible electrical generators contoured to conform to the anatomy of the intercostal space and embedded with electrodes for measuring electrical activity, as well as echocardiographic piezoelectric electrodes for measuring mechanical activity of the heart and Doppler blood flow. The system is equipped with microprocessors to analyze a cardiac situation based on the sensors' readings, produce a diagnosis, and generate the therapeutic strategy, such as "pacing or shocking pulse" in a life-threatening situation, or "observe" in non-life-threatening situations, meanwhile providing a bedside instantaneous on-demand display of the heart rhythm and the system's functionality through the patient's skin.

26 Claims, 10 Drawing Sheets

IMPLANTABLE PACING AND DEFIBRILLATION SYSTEM WITH ILLUMINATED GENERATORS

REFERENCE TO RELATED APPLICATIONS

This application is a Continuation-in-Part of patent application Ser. No. 15/691,924 filed on 31 Aug. 2017, which is a Continuation-in-Part of the patent application Ser. No. 15/042,301 filed on 12 Feb. 2016, which is a Continuation-in-Part of the patent application Ser. No. 13/649,792, filed on 11 Oct. 2012, now U.S. Pat. No. 9,289,593, issued on 22 Mar. 2016.

INCORPORATION BY REFERENCE

Patent application Ser. Nos. 15/691,924 and 15/042,301, and U.S. Pat. No. 9,289,593 are hereby incorporated by reference.

FIELD OF THE INVENTION

The present application relates to the field of cardiology, and in particular, to an implantable pacemaker and defibrillator (ICD) system equipped with a miniature generator implantable in the intercostal region of a patient's body and capable of generating light signals corresponding to the cardiac situation and the system operational parameters, where the light signals are transmitted through the skin and can be visible external to the skin overlaying the implanted generator.

The present invention also relates to a method and system for the extravascular cardiac stimulation and defibrillation which utilizes dual illuminated generators embedded with electrical and ultrasound/Doppler electrodes implanted within the intercostal space in the left hemithorax of a patient and capable of sensing, pacing and shocking the heart.

More in particular, the present invention is directed to the treatment of symptomatic bradycardia using subcutaneous generators surgically or percutaneously implanted in the intercostal space in proximity to the heart of a patient to provide electrical cardiac pacing which does not require trans-venous leads.

In overall concept, the present invention is directed to implantable pacemaker and/or defibrillator equipment operating with internal generators which use one or more Light Emitting Diodes (LED), organic LED's (OLED), or active Matrix Organic LED's (AMOLED), and a liquid crystal display (LCD) embedded in the front facing surface of the system and positioned in close proximity to the skin of a patient, where colored light visible signals emitted by the LEDs (and transmitted to the LCD) reflect physical patient cardiac parameters and/or equipment operation parameters (which may include the rate and the rhythm of the heart, the battery status of the generators, as well as the status of the low and high voltage discharges to the heart produced by the generators), so that the light signals generated by the LEDs and displayed on the LCD can be seen through skin of the patient. The display of the signals may be automatically activated, or may be intermittently activated by tapping on the generator(s), as well as by changes in the patient's body position and/or his/her activities.

Furthermore, the present invention relates to an extravascular pacemaker system operating to provide a high and a low voltage pacing of cardiac tissues responsive to readings of sensors employed in the system, where the sensors are capable of detection of the heart electrical parameters, Doppler cardiac/vascular blood flow, and echocardiographic mechanical cardiac activity.

In addition, the present application relates to an extravascular pacemaker system equipped with a flexible generator implanted beneath the skin of the patient in the intercostal space of a patient's body for a low voltage pacing of cardiac tissues free of interference with the sternum and ribs.

Moreover, the present invention addresses an extravascular pacemaker system for pacing cardiac tissues by means of a miniature generator implant that is rechargeable from a power source external to the chest wall through inductive charging capable of wireless transfer of energy from the external power source to the generator's battery for repleting the battery when needed.

The subject invention further relates to a system for sensing myocardial electrical signals from an extravascular location in close proximity to the heart and for providing low voltage pacing or high voltage defibrillation responsive to the sensed cardiac situation.

Still further, the subject invention is directed to a pacemaker defibrillator system configured for stimulation of cardiac tissues using electric and/or ultrasound electrodes, and adapted for simultaneous shocking of cardiac chambers facilitated by two or more defibrillation electrodes attached to two or more generators.

The present invention also is directed to a pacemaker defibrillation system equipped with multiple extravascular generators which are capable of sequential stimulation of the atrium, His bundle (part of the primitive interventricular septum), as well as the right and left ventricles, with the help of a piezoelectric crystal which provides physiologic pacing needed for treating heart failure.

Moreover, the subject invention is directed to a pacemaker defibrillator system which operates based on an algorithm for heart stimulation and which uses mechanical sensors of cardiac motion and the Doppler blood flow (such as operating with ultrasound/Doppler piezoelectric crystals), as well as electrical sensors, and upright body position sensors, in order to detect and verify the presence (or absence) of life-threatening arrhythmias, which is beneficial for minimizing (or excluding) the risk of inappropriate cardiac shocks.

In addition, the subject invention is directed to a pacemaker defibrillator system which utilizes two or more implanted flexible generators with two or more pacing electrodes and two or more defibrillation electrodes, which are implanted, as an entire unit, within the left intercostal space in close proximity to the heart of the patient in order to increase the likelihood of successful defibrillation.

The present invention also addresses a pacemaker defibrillator system which is capable of distinguishing between a false alarm and a life-threatening cardiac situation by using a position sensor that detects a patient's upright posture indicative of a non-life-threatening situation and requiring a disablement of the defibrillation pulsing.

BACKGROUND OF THE INVENTION

Sudden cardiac death is a preventable catastrophic event that claims more than 300,000 lives each year, or about 1,000 people every day, 95% of whom do not make it to a hospital with possible catastrophic results. In patients at increased risk of cardiac arrest, implantable cardioverter defibrillators can prevent sudden death.

Subcutaneous implantable cardiac defibrillators are needed to provide defibrillation therapy to terminate life-threatening ventricular arrhythmias such as ventricular fibrillation for patients in whom standard transvenous defibrillators are not suitable, such as for patients who lack adequate venous access. The subcutaneous generators sense electrical cardiac activity by electrodes placed over the sternum or ribs, or by the generator itself.

Unlike transvenous systems where the electrical cardiac signal is consistent due to the fact that electrodes contact the lining of the heart chambers, the subcutaneous leads detect cardiac electrical activity from a distance and may have suboptimal electric signal in up to 10% of patients using electrodes anterior or along the body of the sternum. Without an adequate signal, generators are unable to detect electrical cardiac activity. This typically results in inappropriate shocks.

In addition, subcutaneous implantable cardiac defibrillators are not indicated for patients with slow pulse who require cardiac pacing, and patients with ventricular tachycardia who may benefit from anti-tachycardia pacing. In addition, unipolar stimulation and impedance-based features are contra-indicated.

Conventional cardiac pacemakers and defibrillators are generally equipped with a generator for electrical stimulation that is implanted in a patient's body outside the thoracic cage for cardiac pacing and defibrillation. If ventricular fibrillation is sensed by the device, it delivers high voltage shocks to the heart using electric leads within or in close proximity to the heart. Subcutaneous implantable cardioverter defibrillators require more energy (75-80 Joules) compared to transvenous systems necessitating larger generators, more storage capacitors and limited ability to deliver anti-tachycardia pacing for life-threatening ventricular tachycardia.

Conventional subcutaneous Implantable Pacemaker and Defibrillators (ICDs) are equipped with generators placed outside the thoracic cage over the ribs along the lateral chest wall. The generators are typically connected by wires to vertically oriented defibrillation electrodes lying over the sternum, or alongside the lateral edge of the body of the sternum over the ribs and costal cartilages. A second defibrillation electrode may also be used which is inserted into the anterior mediastinum behind the sternum.

Conventional systems require wires extending from the generator in the lateral chest along the anterior chest to the sternum. The impedance of the sternum and ribs is higher than that of the muscles of the intercostal space or the lungs. This is in part due to a low water content of bones (<33%) and a high electric impedance of fat present in the ribs, sternum and the bone marrow. Intercostal muscles and lungs conduct electricity with less impedance than bones due to a higher water content (>75%).

In addition, up to 10% of patients may not have an adequate electrocardiographic signal for the ICD sensing and may not be eligible for conventional subcutaneous ICD due to the distance of the electrodes from the heart.

There are numerous conditions which would preclude the implantation of conventional transvenous pacemaker/defibrillator systems, such as a compromised venous access, the need to preserve veins for hemodialysis, venous thrombosis, patient's history of infection, or the need for indwelling venous catheters. The electrodes carrying the electric impulse are typically secured to the lining of the heart chambers. The pacemaker microelectronics contain circuits and antennas that communicate percutaneously (noninvasively) with external programming transceivers commonly used to interrogate stored pacemaker data and reprogram pacemaker function as deemed appropriate.

A number of implantable pacemaker and defibrillator systems has been developed and used for cardiological purposes. For example, Marshall, et al. (U.S. Pat. No. 10,137,295) presents an extravascular implantable defibrillator with a coil electrode and pace/sense electrodes positioned over the ventricles.

Referring to FIGS. 1A and 1B, Marshall's implantable defibrillator system 10 includes a generator 12 positioned along the left lateral chest wall overlying the ribs 14 with wires 16 extending subcutaneously to two shocking electrodes 18, one alongside the sternum overlying the ribs and the second beneath the sternum in the anterior mediastinum, configured for generating shock pulses and sensing electrical signals from the heart 20.

As shown in FIG. 1B, the length of the electrical path 28 between the generator 12 and the shocking electrodes 18 is large due to the intervening ribs, and the impedance to the flow of electricity across the chest is undesirably high due to the length of the electrical path 28. In addition, the intervening tissues (ribs, sternum, etc.) between the generator 12 and the shocking electrodes 18 may introduce an adverse effect, distorting the electrical signals. It is desirable to attain a shorter length of the electrical path across the intercostal (commonly, $4^{th}$ or $5^{th}$) space to be closer to the left ventricle, and to avoid intervening ribs or sternum in the electrical path.

The feasibility of an entirely subcutaneous implantable cardioverter defibrillator was presented by Brady, et al., in New England Journal of Medicine, 2010; 363:36-44. These extravascular systems, as well as other conventional implantable generators, are not however adapted for instantaneous display of signals corresponding to the heart rate and rhythm, as well as the battery status and generator function, which would be visible through the patient's skin overlying the implanted generators.

Recharging of implanted devices (such as the artificial heart and cardio pacemakers) remains a serious problem in the field of cardiology. Wireless recharging is preferably used for the battery recharging. For a wireless cardio implant system, it is desirable that generators detect and induce electrical and mechanical action. Conventional generators are generally disk-shaped and may not be suitable for operability in close proximity to cardiac tissue.

Rechargeable cardiac pacemakers using nickel-cadmium and zinc-mercuric systems are disclosed, for example, in U.S. Pat. Nos. 3,454,012, 3,824,129, 3,867,950, 4,014,346, and others. These pacemakers contain a charging circuit energized by electromagnetic induction from an external source. The "electromagnetic induction" generates current in the pacemaker's charging circuit that is converted to a direct current voltage to charge the battery.

These systems are prone to various problems due to frequent charging. Specifically, these pacemakers may suffer from memory effects that can lead to reduction of the battery capacity after each recharge, as well as poor specific energy density, low cell voltage and liberation of hydrogen gas. In order to obviate the inherent limitations of the zinc-mercuric oxide and nickel-cadmium battery cells, lithium batteries were introduced which are described, for example, in U.S. Pat. No. 5,411,537.

Ideally, electrical energy is transmitted through the skin of a patient between a transcutaneous energy transfer device and an implanted medical device. For example, U.S. Pat. No. 5,350,413 teaches a transcutaneous energy transfer device using an external primary coil located outside the skin, and a secondary coil implanted under the skin. The primary coil induces current in the secondary coils, thus forming a transformer.

Wang, et al. (U.S. Pat. Nos. 5,690,693 and 5,702,431) presents an improved transcutaneous energy transmission to charge rechargeable batteries in implanted medical devices. The system comprises a primary coil resonant circuit and a secondary coil attached to the medical device. A sinusoidal waveform current is generated by operating two solid state switches (turned OFF and ON) and is applied to the primary coil and a capacitor to induce a current that recharges the battery in the medical device.

Wang addresses an alignment mechanism in the recharging device, which does not need extra components in the implanted device except for the components used for charging. Wang's energy transmission system minimizes the size of the receiving coil and permits positioning of the coil inside the housing of the implantable device.

Brownlee, et al. (U.S. Pat. No. 4,332,256) presents a system for telemetering and testing the functions of an implanted pacemaker from a remote location.

Wang, et al. (U.S. Pat. No. 7,982,370) discloses a miniature electrical generator with piezoelectric fine wire extending along the surface of an elongated substrate. The piezoelectric nanowires extend radially to generate electricity.

Plug, et al. (U.S. Pat. No. 9,406,826) presents a flexible electrical generator consisting of at least one photovoltaic device attached to a flexible support made of high strength polymeric semi-crystalline fabric.

Sabi, et al. (U.S. Pat. No. 9,673,481) introduced a thin film solid state lithium battery with an electric insulating substrate.

Using "wireless power transfer," the EM (electro-magnetic) energy may be transmitted from an outside source to the generator embedded beneath the skin. Such feature is desirable in order to minimize the size of conventional generators which are usually bulky and are not ideally suitable for implantation into a patient's body.

It would be highly desirable to provide a miniature generator well-suited for implantation into the patient's body having a prolonged battery life.

In defibrillators' operation, an appropriate shock should be produced and delivered to the heart. The appropriate shock is defined as a shock delivered for a life threatening arrhythmia, such as ventricular tachycardia or ventricular fibrillation.

Among patients with heart failure who are implanted with ICD for primary prevention of sudden cardiac death, some patients experience inappropriate (false) shocks, i.e., the shocks erroneously generated in a situation of a non-life-threatening arrhythmia, which may cause a devastating psychologic impact. Inappropriate electric shocks constitute a major problem in arrhythmia detection algorithms in implantable cardioverter defibrillators. They may cause supraventricular tachycardia, QRS and T wave double sensing, electromagnetic interference, diaphragmatic sensing, or may be related to lead fracture, insulation break, or lead dislodgment.

Rhythm discrimination is conventionally performed based on the analysis of the electrocardiographic waveforms. Theuns, et al. (Europace, 2001; 3:181-186) proposed the addition of the atrial sensing to the ventricular sensing in order to improve the discrimination methodology between the ventricular and the supraventricular arrhythmias.

All conventional algorithms for pacing/shocking use a routine for sensing cardiac electric activities to determine delivery of shocks to the heart.

However, conventional systems do not take into account the presence or absence of ventricular wall motion as detected by echocardiographic sensors, or blood flow as detected by Doppler sensors. This may lead to false results of the analysis, and in extreme cases, is dangerous to the patient's wellbeing.

Sweeney, U.S. Pat. No. 6,654,683, describes an ultrasonically activated implantable cardiac electrode system for ultrasound pacing of cardiac chambers using piezoelectric crystals embedded in heart and transvenous leads. The piezoelectric elements convert mechanical energy into electrical energy which is sufficient to cause pacing of the cardiac tissue. Mechanical energy may originate from an external source low frequency ultrasound transmitter. The electrical energy produced by the piezoelectric element delivers pacing level electrical energy between the system's anode/cathode. The system is also equipped with active fixation elements using tines, hooks, and barbs.

The system presented in the U.S. Pat. No. 6,654,683 disadvantageously fails to address the use of a leadless flexible curvilinear ultrasound generator or application of the ultrasound energy to the heart directly from a source implanted in the intercostal space to induce electrical stimulation of the heart tissue which may or may not require imbedded piezoelectric elements.

Lee, US Patent Application Publication No. 2004/0167416, discloses an implantable monitor with hemodynamic and acoustic sensors, memory unit to store data, and a microprocessor. The rectangularly shaped device is implanted beneath the skin overlying the heart. The device may rest against a bony tissue in order to provide enhanced phono-cardio-graphic acoustics with ultrasound sensors positioned over bony tissue of an intercostal space. Alternatively, in order to avoid a patient discomfort, the monitoring device may be placed away from the rib cage, for example, in the pectoral region. Disadvantageously, the Lee system is solely for monitoring purposes, and neither is designed, equipped or suitable for pacing or shocking, nor is it adapted for implantation in the intercostal space of a patient.

Marcovecchio, US Patent Application Publication No. 2016/0067479, is a cardiac pacing lead delivery system in which a rigid generator is secured to the sternum, while a lead advancer passes perpendicularly to the intrathoracic structures through the intercostal space in close proximity to the heart. Disadvantageously, Marcovecchio system is not a leadless system and is not adapted for being implanted in the intercostal space of a patient.

The intercostal region would be an ideal location for implanting a pacemaker/defibrillator because it can provide proximity to the ventricles without intervening sternum or ribs. However, none of the conventional pacemaker systems have been adapted for positioning in the intercostal region of a mammalian body.

A compact electrical generator operating with double-action electrodes attached to the generator would be desirable if configured to conform to the intercostal space configuration for being embedded therein in close proximity to cardiac tissue for sensing electrical heart pulses, as well as the heart wall motion, and Doppler blood flow, and capable of providing transfer of electrical/ultrasound/Doppler/infrared and/or magnetic stimulation signals to the heart responsive to the sensed cardiac parameters without interference from sternum or ribs.

Another shortcoming of the conventional pacemaker/defibrillator systems is that they do not operate in accordance with an algorithm for determining the timing and sequence of stimulation of cardiac tissues based on additional sensing of mechanical cardiac motion and blood flow sensed by the ultrasound echocardiography and Doppler flow to reduce the risk of inappropriate shocks.

Conventional pacemaker defibrillator generators permit sensing electrical cardiac activity by use of electrodes embedded into the endocardium or vascular structures of the heart. Without electrodes, generators in conventional pacemakers are unable to detect electrical cardiac action.

It would be highly desirable to provide a pacemaker which does not require insertion of the electrodes into the endocardium or vascular structures of the heart.

Conventional pacemakers and defibrillators generally use disc shaped generators implantable outside the patient's thoracic cage. The disc shaped generators used for extravascular defibrillators are placed overlying the ribs along the left axillary lines. There are no conventional pacemakers which would be equipped with a flexible generator, having a curved configuration along its longitudinal axis, and which would have a low profile to accommodate the contour and dimensions of the intercostal space for being inserted percutaneously, and which would be easily rechargeable.

It would be highly desirable to provide a generator having a curvilinear elongated shape adapted to conform to the intercostal space (the space between the ribs of the chest overlying the heart) configuration which would permit sufficient proximity to cardiac structures for effective leadless transfer of electrical, ultrasound, Doppler, infrared and magnetic stimulation signals between the generator and the heart of the patient, and which would be capable of providing bedside instantaneous continuous visual multicolor display of heart rate and rhythm, diagnosis of pulseless electrical activity (PEA), pacing and shocking status of the generator, as well as the battery level, without the need for an additional testing equipment and expert personnel to interrogate the generator.

No conventional implantable generators provide instantaneous visual display data regarding the heart rate, rhythm and function, as well as the status of the battery and continuous pacing and shocking data, which could be conveniently seen through the patient's skin overlaying the implanted generator.

It would be highly desirable to provide a subcutaneous system capable of generating instantaneous visible signals corresponding to the heart rate, heart rhythm and heart function using LCDs and multicolored LEDs embedded underneath the skin, that would receive continuous recordings using electrodes positioned close to the heart without intervening from the sternum, ribs or fat, and without invasion of the mediastinum. Such readings would preferably include ultrasound and Doppler parameters of the heart functions and the patient's body position to confirm the presence or the absence of life-threatening arrhythmias to provide a reliable anti-tachycardia pacing of ventricular tachycardia.

It would also be desirable to provide a pacing and subcutaneous defibrillation system equipped with multiple generators and electrodes extending from the base of the heart to the left ventricular apex in order to reduce shock impedance.

SUMMARY OF THE INVENTION

It is therefore an object of the present invention to provide a subcutaneous pacemaker defibrillator system equipped with flexible miniature generators adapted for being implanted within the intercostal space of a patient's body in proximity to the heart and equipped with light signals generating and/or displaying means and underlying the skin of the patient in close proximity and facing positional relationship thereto, so that the light signals generated and displayed at the surface of the generators are transmitted through the patient's skin overlaying the implanted generators and can be visible external to the patient's body.

It is another object of the subject invention to provide a subcutaneous pacemaker defibrillator system utilizing generators equipped with LEDs, or OLEDs, or AMOLEDs, and LCD(s) embedded on the surface of the generator in the skin facing position to generate visual light signals indicating cardiac activity parameters and system's operational state, which are transmitted and visible through the skin overlying the generators.

It is a further object of the present invention to provide a subcutaneous pacemaker defibrillator system operating under control of a microprocessor and equipped with an LCD and LEDs generating light signals, the colors of which are determined by the input(s) from the microprocessors that receive and process continuous data from electric, echocardiographic and Doppler sensors, and determine: (a) the presence of a normal heart rhythm, which is subsequently displayed on the LCD as a pulsating green signal, or (b) an abnormal heart rhythm, which can be seen on the LCD as pulsating yellow signals, or (c) the absence of the heart rhythm, which can be indicated on the LCD as a steady red signal, or (d) the absence of wall motion and Doppler blood flow (with the presence of electric activity) which can be seen on the LCD as a pulsating red signal, or (e) a low voltage pacing which is shown on the LCD as a pulsating blue signal, or (f) a high voltage shock which may be seen on the LCD as a steady blue signal for about 3 seconds, and (g) a low battery generator status which is indicated on the LCD as a steady yellow signal alternating with the signal absence. In some embodiments of the subject system, the LEDs and LCDs may operate continually. In alternative embodiments, they may be activated by tapping on the generator, or by changing the body position or the patient's activities.

An additional object of the present invention is to provide a pacemaker defibrillator system equipped with two or more flexible generators having a low profile (flat) elongated structure conforming with the anatomy of the $4^{th}$ or $5^{th}$ intercostal spaces and suitable for being implanted therein. This would allow stimulation of the heart (from the base to the apex) directly by utilizing electric leads located within the inner surface of the generators in the intercostal region in close proximity to the heart.

Furthermore, it is an object of the present application to provide a pacemaker defibrillator system equipped with a miniature generator which is adapted for a wireless recharging of the generator's battery from an external power source.

It is still a further object of the present invention to provide a pacemaker defibrillator system operating in accordance with an algorithm which takes into account (in addition to the electrical activity of the heart) the presence, or absence, of the echocardiographic ventricular wall's motion and function, as well as the Doppler blood flow and the patient's body position, and which ensures correct readings and analysis of the cardiac situation to prevent generation of inappropriate electrical signals (false shocks/pulses) that may be harmful to the patient well-being as the false shocks/pulses may increase the chance of a patient's adverse outcome.

An additional object of the present invention is to provide a pacemaker defibrillator system which uses echocardiographic and Doppler sensing, as well as blood flow readings in the analysis of the heart function to detect presence or absence of the life threatening heart rhythms.

It is a further object of the present invention to provide an implantable pacemaker defibrillator system which is capable of the sensing, pacing, and shocking of various cardiac tissues, supported by two (or more) generators that are equipped with electric and ultrasonic elements capable of sensing the electrical and mechanical activity of the heart (from the heart base to the heart apex), as well as the Doppler blood flow signals from the heart of a patient for correct diagnosis of the cardiac condition.

Furthermore, it is an object of the present invention to provide a pacemaker defibrillator system having a generator embedded into the patient's body in close proximity to the heart from the base to the apex and equipped with double-action electrodes capable of sensing the electrical and mechanical activity of the heart. The double-action electrodes deliver electric and ultrasonic pulses directly to the heart when triggered by the generators' microprocessors which are configured for making a diagnosis based on the sensors' readings.

It is also an object of the present invention to provide a pacemaker defibrillator system equipped with two or more generators which supply electrical energy supporting the functionality of electric sensors and defibrillator leads, as well as ultrasound piezoelectric crystals and Doppler sensors which operate to sense the electrical and mechanical function of, and the Doppler blood flow from, the heart. The ultrasound transducers may deliver high ultrasonic energy directly to the heart to stimulate the base and the apex of the left ventricle when triggered by the generator's microprocessors. The ultrasound transducers may also deliver high ultrasonic energy to deform piezoelectric crystals embedded in various cardiac chambers such as in the coronary sinus, atria or His bundle, to be stimulated when triggered by the generators' microprocessors.

It is still an object of the present application to provide a subcutaneous extravascular cardiac implant system equipped with a flexible, curved, elongated and low-profile (flat) easily rechargeable generator adapted for insertion into the intercostal space of the chest to be in close proximity to cardiac structures which is beneficial for the effective and reliable pacing of the heart tissues using the electrical leads and ultrasound elements and for defibrillation free from the interference from anatomical structures having a high electrical impedance, such as the sternum and ribs.

Also, it is an object of the present invention to provide a pacemaker defibrillator system operating in accordance with an algorithm for triggering a defibrillation action based on the patient's body position and mechanical heart activity, as well as the Doppler blood flow, in addition to the heart's electrical activity.

In one aspect, the present invention is directed to a system for generating and sensing electrical energy transmitted to and from tissues within a mammalian body. The present system, for example, a cardiac pacemaker defibrillator system, includes:

a flexible tube-like elongated shaft (also referred to herein as a shield) configured for being implanted within the intercostal space between the ribs of the chest chamber of a patient. The system flexible shaft (shield) has an elongated low-profile curved body which is adapted for implantation within the patient's intercostal space percutaneously or surgically. The flexible shaft of the subject generator may be formed of an electrically conductive EMI/RFI shielding composition and is contoured to be congruent with a shape and dimensions of the intercostal space envelope in the chest chamber.

The subject system further includes at least two flexible electrical generators (capable of sensing and producing electrical and ultrasonic energy) embedded within the flexible shaft; and a number of double-action electrodes embedded with each generator. When the generators are implanted in the intercostal region, the electrodes are disposed in a close proximity to, and in facing position with the heart of a patient.

The generators in the subject system are equipped with light emitting diodes (LEDs) and a light displaying unit, such as, for example, a liquid crystal display (LCD). The generators (and the generators shaft) are implanted in the intercostal space with the LEDs and the LCD positioned in close proximity to and in facing relationship with, the skin overlaying the implanted generators. The signals generated by the LEDs and the LCD are made visible through the generators shaft.

When the LEDs generate light signals, and/or the LCD displays light signals (in various format), the light signals are transmitted through the patient's skin and are visible externally to the skin overlaying the generators.

The light signals visible via the skin are reflective of the cardiac condition, various parameters of the heart activity, mode of the system operation, therapy state, as well as the system's operational parameters.

The generators' electrodes used in the subject system operate based on various physical principles and are configured for a double-action operation, i.e., both capable of (a) sensing the heart activity (electrical and mechanical activity of the heart, as well as blood flow from the heart), and (b) delivery of stimulation pulses to the heart when needed.

The generators' electrodes may include at least one piezoelectric crystal embedded within (or positioned circumferentially of) the generators (or the generator's shield) and are disposed in a facing position with the heart of the patient when implanted in the intercostal space. The piezoelectric crystals are configured as echo sensors to perform measurements of mechanical heart function by continuous and pulsed Doppler echocardiographic signals for diagnostic purposes.

In addition, the generators are equipped with an internal ultrasonic source which allows the generators to deliver high energy ultrasonic bursts directly to the heart tissue for therapeutic purposes to stimulate the heart when commanded by the generators' microprocessor(s).

The subject electrical generators are configured to detect, as one of their functions, the electrical activity of a patient's heart. For this purpose, the generators' electrodes include at least one electrically conductive electrode attached to each generator or the generator's shaft for sensing the heart's electrical activity.

The subject generators are also configured to provide high voltage shock and low voltage pacing via the electrically conductive electrodes.

The echocardiographic sensors are capable of operating with the pulsed, as well as continuous, Doppler ultrasound signals to detect mechanical heart function, or the lack thereof. The generators are further equipped with the embedded ultrasound and Doppler sources in proximity to the echo electrode to support the direct pacing operation.

The subject generators produce electric and ultrasonic pacing (or shock) pulses responsive to the combined readings corresponding to electrical, as well as mechanical, activities of the heart tissues, and the blood flow readings acquired to diagnose a life-threatening heart rhythm.

The subject generators are adapted for wireless recharging of the generator's battery as well as the generators' ultrasonic power source. For this purpose, the generators are equipped with receivers and receiving antennas for wireless power transfer from external power sources and from external ultrasonic energy generators.

The subject generators further include microprocessor(s) which are configured with an input for receiving the readings from the electrically conductive electrodes and the echocardiographic electrodes which are adapted to run on the algorithm for determining the presence of electro-mechanical dissociation based on the electrical and mechanical signals from the heart to diagnose a life-threatening heart rhythm.

The generators' electrodes, echocardiographic sensors, or the blood flow as detected by Doppler sensors, as well as the body position sensors, transmit data to the microprocessors to confirm the presence of the non-life-threatening heart rhythm based on the electrical and mechanical signals from the heart to avoid generation of inappropriate pacing shocks.

In another aspect, the present invention is directed to a method for sensing and generating energy transmitted from and to the heart of a patient. The subject method is accomplished by:
  forming flexible elongated low-profile curvilinear generators,
  attaching at least one parameter sensing electrode to the flexible generators,
  embedding the flexible generators in a flexible shaft contoured to conform to the intercostal space of a patient, and
  implanting the flexible generators embedded in the flexible shaft in the intercostal space of the patient with the at least one parameter sensing electrode in facing positional relationship with the heart of the patient.

The method further continues by:
  operatively coupling a microprocessor to the generators (alternatively, the microprocessor can be embedded in the generator structure);
  sensing parameters of the heart activity with the at least one parameter sensing electrode;
  transmitting the sensed parameters to the microprocessor for being processed.

The microprocessor in the subject generator operates based on a routine which includes:
  analyzing the sensed parameters;
  producing a diagnosis of the cardiac situation;
  forming a control signal based on the computed diagnosis of the cardiac situation; and
  transmitting the control signal to the generator to produce a pacing signal if the sensed parameters are indicative of a life-threatening heart condition.

The subject method further continues by:
  embedding piezoelectric crystals in the flexible generators, and
  measuring the mechanical heart activity by the piezoelectric crystals; and
  embedding electrically conductive electrodes in the flexible generators, and
  measuring the electrical heart activity.

The piezoelectric crystals in the subject generators may be configured for serving as ultrasonic transducers forming a Doppler sensor in the flexible generators for measuring the blood flow from the heart.

The subject method further comprises:
  embedding a receiving antenna in the flexible generators,
  positioning a power source external to the patient's body,
  coupling a transmitting antenna to the power source, and
  recharging the generators' battery by wirelessly transmitting electrical power from the external power source through the coupled transmitting and receiving antennas.

The subject method also comprises:
  embedding a source of ultrasonic energy in the generators,
  positioning an ultrasonic energy generator external to the patient's body,
  wirelessly recharging the internal source of ultrasonic energy from the external ultrasonic energy generator, and
  generating pacing ultrasonic pulses by the internal source of ultrasonic energy to be delivered therefrom to the heart subsequent to receiving the control signal from the generator's microprocessor.

One of the core aspects of the subject method is the ability of the subject system's generators to produce light signals which may be reflective of the cardiac condition/situation, heart activity, therapeutic course of actions, mode of the system operation, as well as of various operational parameters of the equipment.

When the generators are implanted in the intercostal region of the patient's body with the light signals producing equipment located in facing relationship and in close proximity to the patient's skin, the visible signals emanating from the generators are transmitted via the skin overlaying the implanted generators and are easily visible externally to the skin by medical personnel. This feature of the subject method allows convenient monitoring of the patient's cardiac condition and the therapy performed, as well as the implanted system's functionality.

These and other objects and advantages of the subject system and method will be apparent from reading the following Detailed Description of the Invention considered in conjunction with the accompanying Patent Drawings Figures.

DETAILED DESCRIPTION OF THE PREFERRED EMBODIMENT(S)

Referring to FIGS. 2A-2B and 3-8, the subject pacemaker and/or defibrillator system 100 is designed for detecting electrical signals, mechanical signals and Doppler blood flow signals from the heart 102, as well as for detecting a patient's body position, and for subsequent generation of electrical pacing stimulation and high energy ultrasound pulses for pacing and electric shock treatment of a patient in the case of the life threatening tachycardia or cardiac arrest.

Figure 2A:
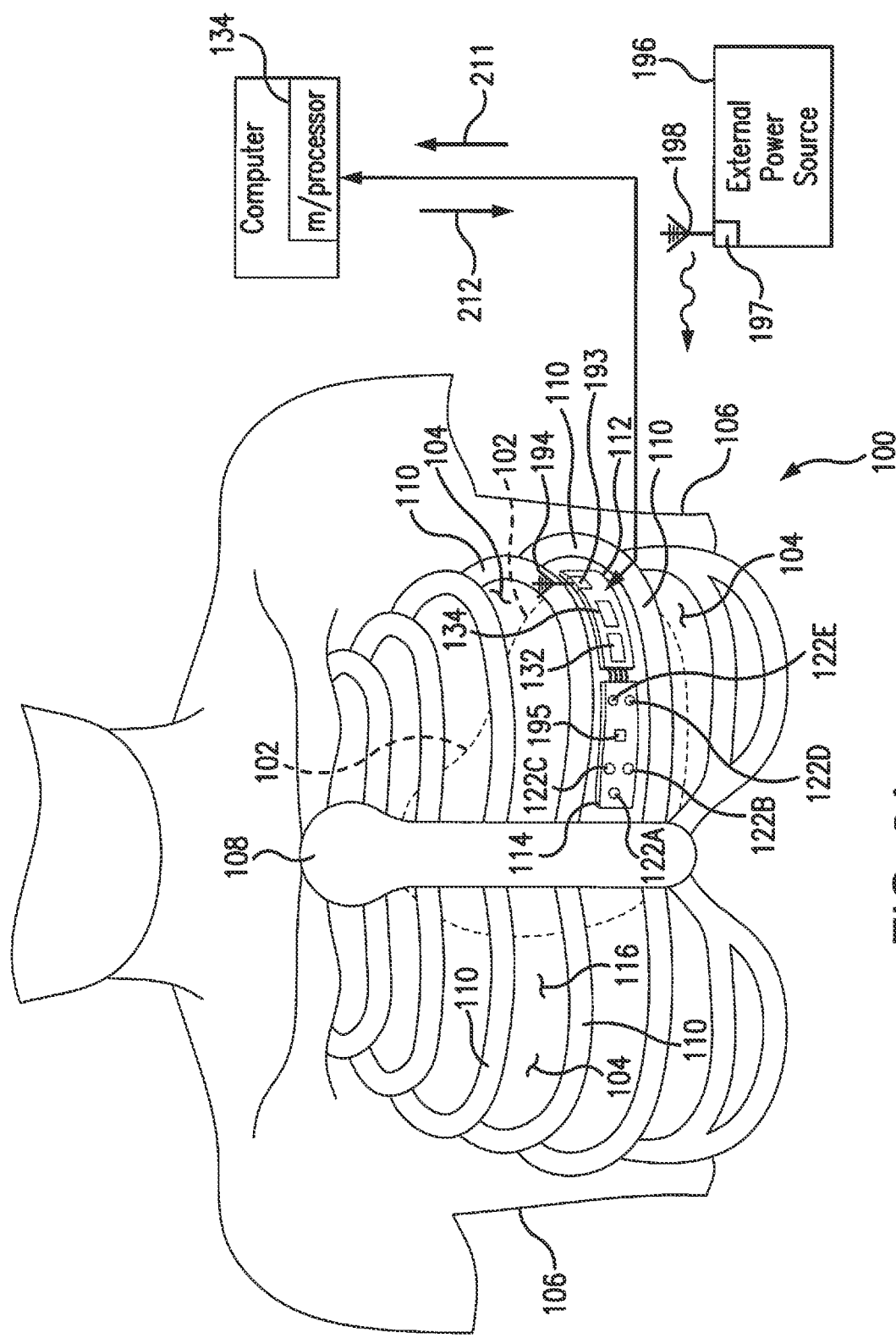
FIG. 2A is a schematic representation of the subject subcutaneous extravascular pacemaker defibrillator system implanted within the intercostal space in the chest cavity showing two generators configured in conformity to the anatomy of the intercostal space.

The intercostal space 104, specifically, the fourth or fifth intercostal space, defined between ribs 110, is positioned in close proximity to the heart of a patient without intervening bony tissues (ribs 110, sternum 108, etc.), and thus is a preferred implantation place for the subject system 100, as shown in FIG. 2A. The intercostal space 104 of a patient's chest wall is selected as an implantation site for the subject system 100 in order to avoid any interference from bony structures, such as sternum and ribs.

The subject system 100 includes two or more generators 112, 114, which are adapted for receipt within the body of a patient (under the chest wall 106), and particularly, in the intercostal region 104 located between the patient ribs 110. As an example, for clarity purposes, but not to limit the scope of the subject system, further description will address the system equipped with two generators 112, 114. However, any number of generators are contemplated in the subject system.

The medial generator 112 and the lateral generator 114, each are formed as a flexible elongated low-profile member adapted to the anatomical contour of the intercostal space 104. Specifically, the generators 112, 114 are formed as curved members which are congruent to the contour of the intercostal space envelope 116. They are connected end-to-end using flexible hinges 118 (best shown in FIGS. 2 and 3).

Figure 3:
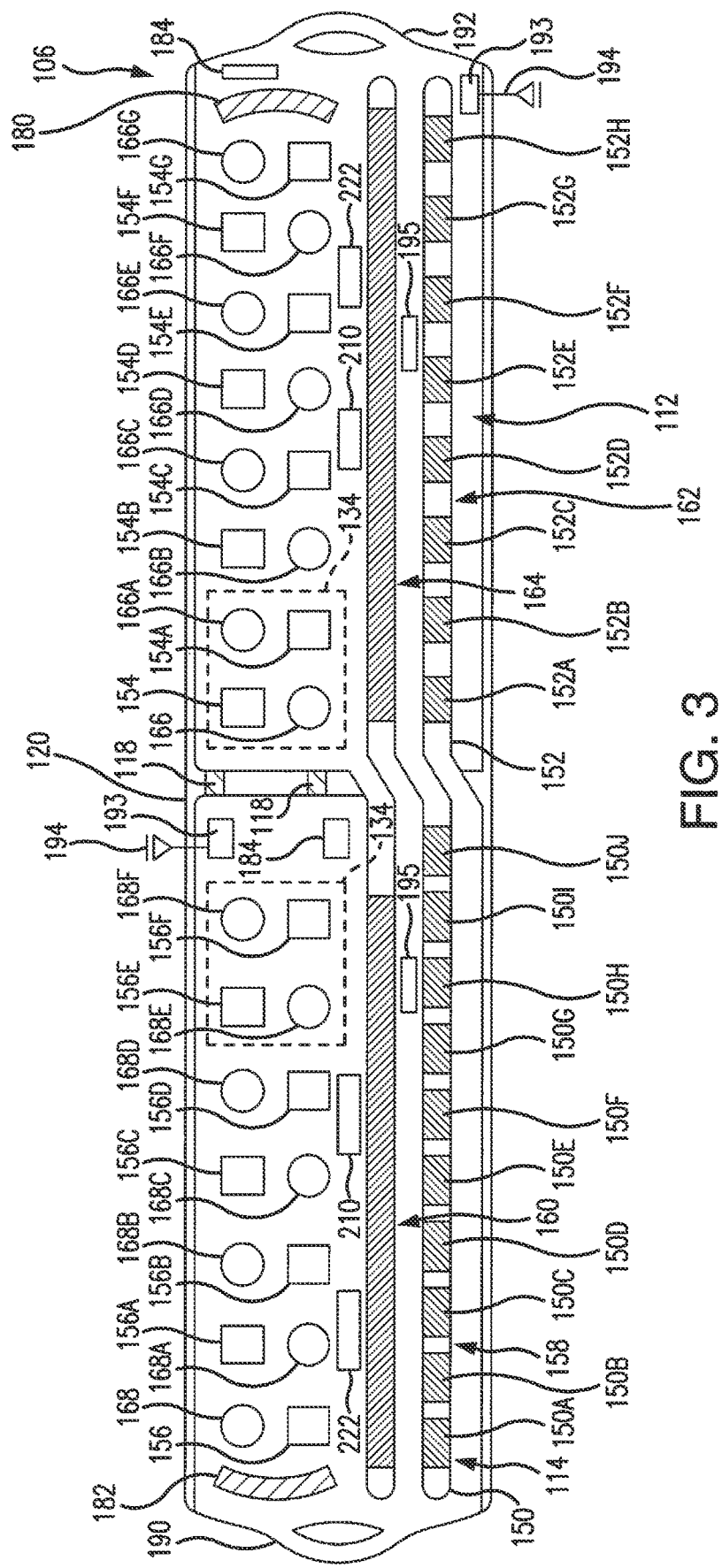
FIG. 3 is a schematic representation of the subject pacemaker defibrillator system illustrating the inner aspect of the system facing the heart comprising electric, ultrasonic, Doppler electrodes configured for sensing electrical, echocardiographic and Doppler signals from the base to the apex of the heart, and for generating pacing pulses (using electric current and high ultrasound energy), as well as shock pulses, with energy derived from both generators to different locations of the heart.

As best shown in FIG. 3, the generators 112, 114 are embedded within a tube-like shaft (also referred to herein as a generator's shield) 120. The shaft 120 is a somewhat tubular member which may, for example, have a somewhat oval contour with a hollow interior to conduct heart signals to the sensors. The generator's shaft 120 constitutes a low-profile (practically flat) curved member preferably congruent to the anatomical configuration of the intercostal space envelope and thus is adapted for implantation in the intercostal space in the chest chamber. An important advantage of embedding the generators 112, 114 within the shield 120 is that, being embedded in the shield 120, the generators 112, 114 are protected from an undesired interference with ultrasonic or electromagnetic signals traveling therearound.

Figure 2B:
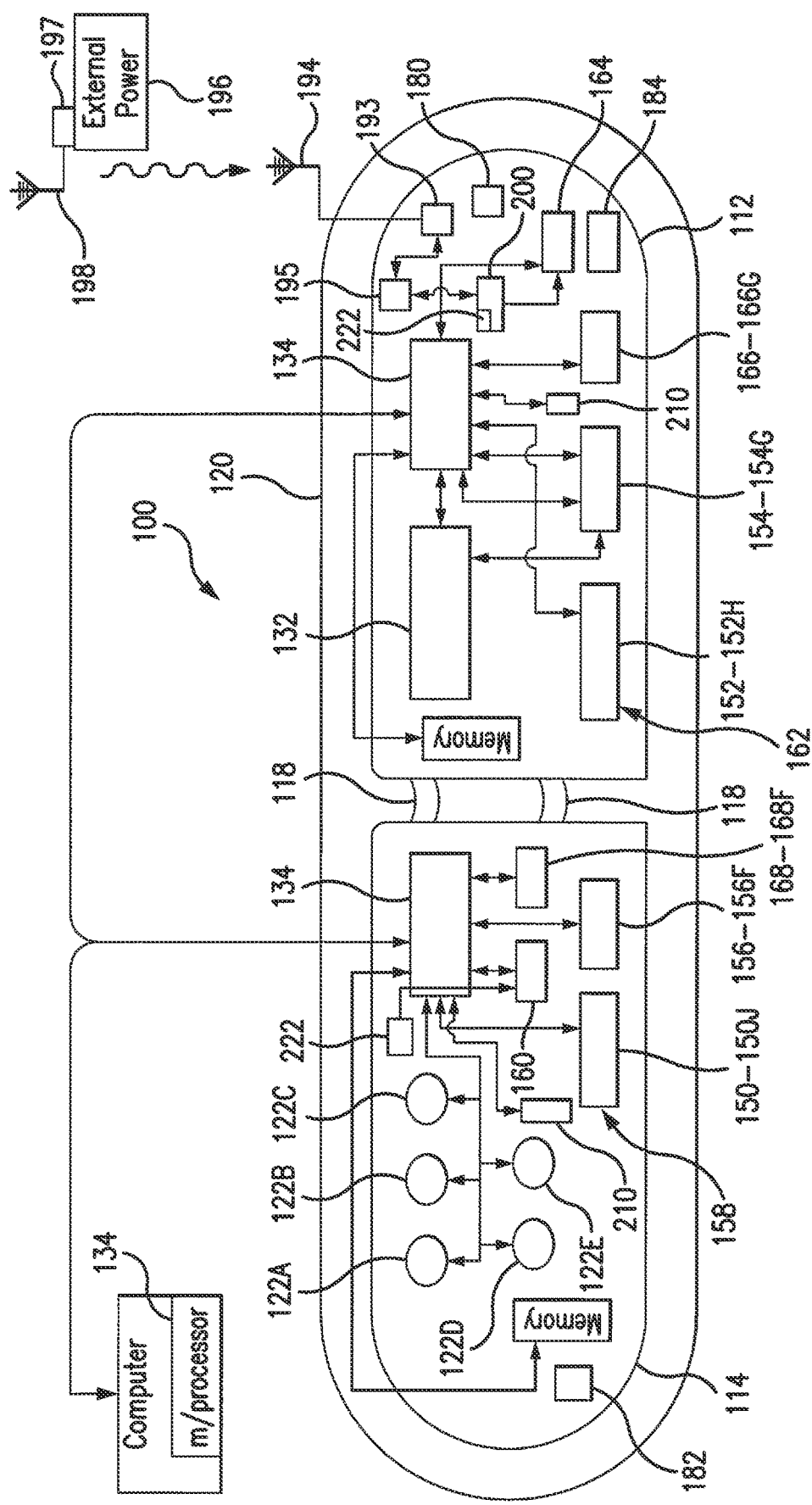
FIG. 2B is a detailed schematic representation of the subject generators depicted in FIG. 2A.

As best shown in FIGS. 2A-2B, multicolor LEDs 122A, 122B, 122C, 122D, 122E, and at least one LCD 132 are embedded in the front surface of the generators 112, 114, respectively, facing the skin of the patient, when implanted. The LED 122A is a multi-colored LED that operates to reflect the instantaneous rate and rhythm of the ventricles; the LED 122B is a multi-colored LED that operates to reflect the instantaneous intrinsic rate and rhythm of the atria of the heart; the LED 122C is a multi-colored LED that reflects the instantaneous intrinsic rate and rhythm of the ventricles of the heart; the LED 122D is a multi-colored LED operating to reflect the instantaneous paced rate and the rhythm of the atria of the heart; and the LED 122E is a multi-colored LED that reflects the instantaneous paced rate and the rhythm of the ventricles of the heart.

Figure 4:
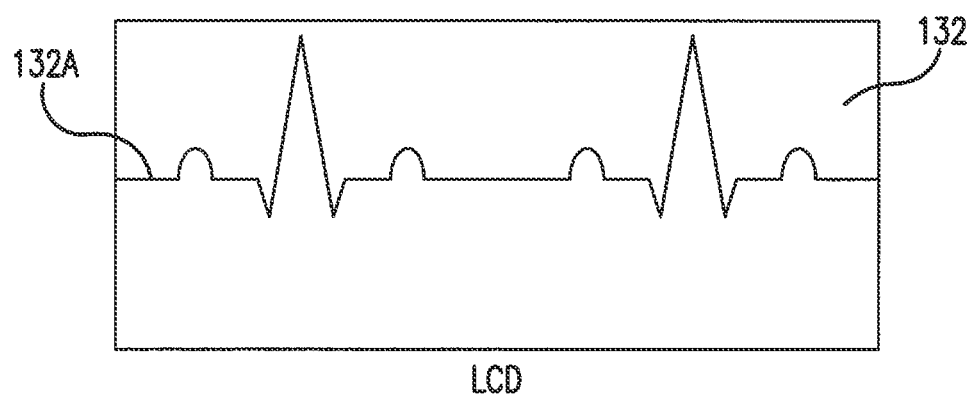
FIG. 4 is a schematic representation of the LCD positioned on the surface of generator(s)

The LCD 132, shown in FIGS. 2A-2B and 4, is a multi-colored LCD that is configured to reflect the instantaneous intrinsic or paced rate and rhythm of the atria and ventricles of the heart.

Being implanted in the intercostal space 104, the generators 112, 114 are positioned with the LEDs 122A-122E and the LCD 132 in facing relationship with and in a close proximity to the skin overlaying the generators 112, 114, so that the light signals are transmitted through the skin and are visible externally to the skin overlaying the generators.

This arrangement provides a mechanism for the medical personnel (or an observer) to conveniently monitor the patient's cardiac situation/heart activity, the equipment functionality, as well as the system mode of operation without a need for an additional data acquiring, interrogating, and/or registering equipment.

In operation, as will be detailed in following paragraphs, the LEDs 122A-122E, under the control of the microprocessor(s) 134 (which may be embedded in one or both generators 112, 114), generate signals of various colors, patterns and sequences (depending on the determined cardiac situation). The signals generated by the LEDs 122A-122E are transmitted and seen through the patient's skin.

Various heart parameters are displayed on the LCD 132, and also can be transmitted and seen through the patient's skin. The visual light signals corresponding to the heart activities are visible through the skin in various colors and patterns. Colors, rates, sequences and patterns of the signals displayed on the LCD 132 may be indicative of the cardiac situation, and help health care professionals to determine the instantaneous rate and rhythm of the heart activity. The signals displayed at the LCD 132 and seen through the skin also may be indicative of the battery status, indicate a normal or an abnormal heart rhythm, generators functions and modes of operation, such as, for example, the pacing or shocking mode of operation, without the need for an additional monitoring or interrogating equipment.

The operation of the LCD display 132 and the LEDs 122A-122E is controlled by the signals produced by the microprocessor(s) 134 based on continuous data received of the microprocessor(s) 134 which correspond to the sensed electric, echocardiographic and Doppler signals, as well as the patient's body position and activities.

In operation, a normal heart rhythm may be indicated by a graph 132A (or some other indicia) on the LCD display 132, or by the LED's light signals (for example, when the LED 122A pulsates before the LED 122B), and can be seen, for example, as a pulsating green signal visible through the skin overlying the generators.

An abnormal atrio-ventricular sequence can be displayed on the LCD screen 132, or may be indicated by the LED pattern (such as, for example, the LED 122B lights before the LED 122A), as, for example, yellow pulsating signals.

A pulsating red signal may, for example, be indicative of the presence of pulseless electrical activity (PEA) in the presence of the heart rhythm (presented on the LCD 132 or indicated by pulsating LED signals), but in the absence of the wall motion and Doppler blood flow.

A steady red signal may, for example, be indicative of the absence of heart rhythm, and the absence of the wall motion and Doppler flow which correspond to cardiac arrest.

A pulsating blue signal may indicate, for example, the low voltage pacing of the heart.

A steady blue signal having a duration of about 3 seconds may indicate a high voltage shock.

A steady yellow signal may indicate the low generator battery situation.

In the absence of colors, different patterns and sequences of light signals representing different heart arrhythmias may be used for the condition interpretation.

The subject system includes a generator's shield 120, which may be formed, for example, from conductive medical EMI/RFI plastic compound materials, polymeric materials with oriented nanotubes, electrically conductive elastomers, plastic substrate sprayed with a metallic ink, etc. A thin flexible layer of biocompatible conductive material capable of flexibly adapting to the contour and dimensions of the intercostal space, or any other dynamically changing space within the patient's body, is suitable for fabrication of the tube-like flexible miniature shield 120.

The generator's shield 120 and the generators 112, 114 are formed as flexible low-profile members contoured in a somewhat curvilinear shape along their length. The generator's shield 120 and the generators 112, 114 are suitable for insertion into the sites of the patient's body having a tortuous contour, such as, for example, the intercostal space. For insertion in the intercostal space, the shield 120 and generators 112, 114 are configured to be congruent with the intercostal space configuration (also referred to herein as the intercostal space envelope) 116.

The generators 112, 114 have been fabricated with a dimensional contour adaptable for insertion and containment within the shield 120. The subject system 100 may, for example, have the following dimensions: about 20-30 cm in length, about 0.5-1.5 cm in width, and about 0.5-1.5 cm in depth, in order to accommodate the intercostal space 104.

The electrically conductive shield 120 along with the generators 112, 114 embedded therein is preferably congruent with the envelope 116 of the intercostal space 104 for being inserted within the intercostal space in proximity to the heart chambers 102 within a patient's body.

The electrically conductive shield 120 may be formed with openings coinciding with the position of the LEDs 122A-122E and the LCD 132 in order to pass the light signals therethrough. Alternatively, the generators shield 120 may carry the LEDs and the LCD on its surface. In this implementation, the LEDs and the LCD positioned on the surface of the shield 120 are operationally coupled to the microprocessor(s) 134 of the generators 112,114 to receive control signals therefrom as well as to the power source of the generators to be powered therefrom. In another alternative embodiment, the shield 120 may be equipped with its own power source to support functionality of the LEDs and the LCD.

The subject system 100 further includes one or more microprocessors 134 (operating in conjunction with control/therapeutic modules) which may be embedded in at least one, but preferably, in both, generators 112, 114.

Figure 5:
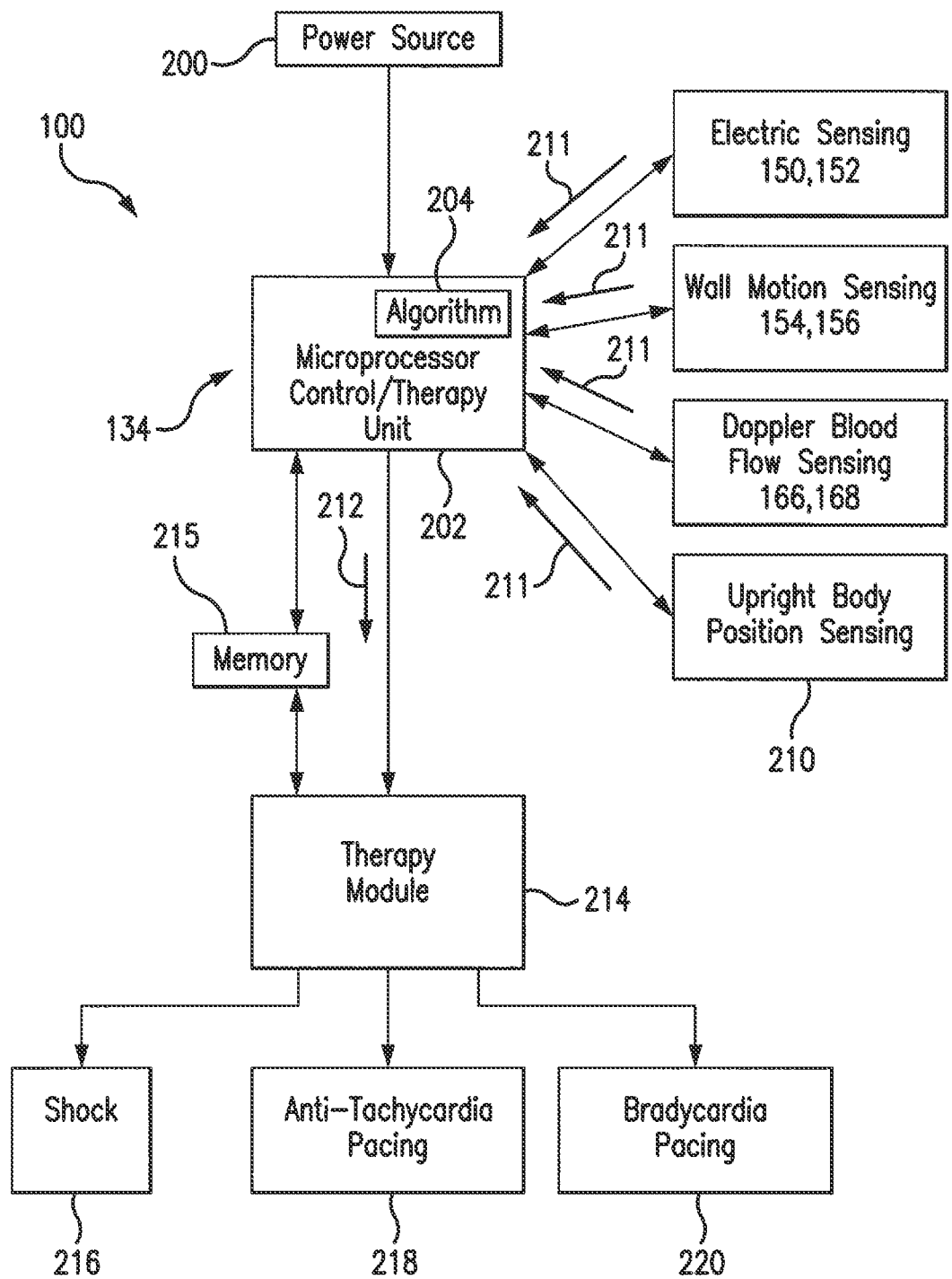
FIG. 5 is a schematic representation of the operational principles of the subject system equipped with the microprocessor control/therapy unit operating to continuously monitor inputs from the EKG electrodes and the piezoelectric sensors regarding electrical, as well as mechanical/Doppler flow activities of the heart, and configured for producing a diagnosis of the cardiac situation.
Figure 7:
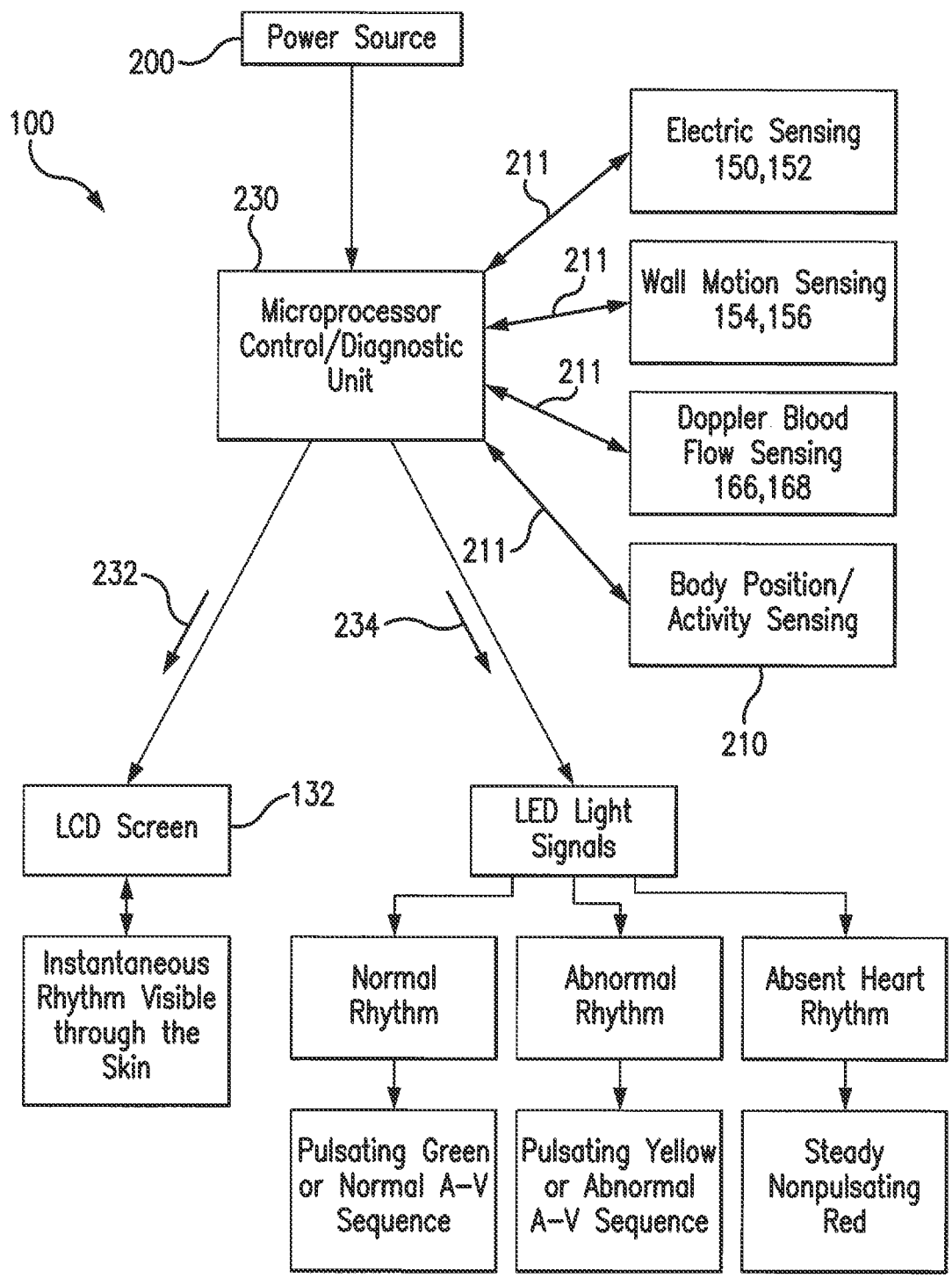
FIG. 7 is a schematic representation of the routine executed by the microprocessor Control Diagnostic unit to control operation of the LEDs and LCD.

Alternatively, the microprocessor(s) 134 may be implemented as external processor unit(s), included, for example, in an external computer (as shown in FIGS. 2A-2B) which may be capable of a wireless communication with the generators 112, 114. A communication path exists between the microprocessor(s) 134 and the generators 112, 114 for the wireless transmission of data 211 corresponding to the heart activity (to the microprocessor(s) 134) and command signals 212 (from the microprocessor(s) 134 to the generators 112, 114, as best shown in FIGS. 2A, 5 and 7.

The generators 112, 114 are equipped with various double-action electrodes. One function of the electrodes is to operate as parameter sensing members. Another function of the electrodes is to generate and deliver to the heart stimulating (shock) pulses, as needed, based on the sensed signals acquired in the sensing mode of operation.

As shown in FIGS. 2B and 3, the double-action electrodes in the subject system may include, for example, electrically conductive electrodes 150, 150A-150J (embedded with the generator 114), and electrically conductive electrodes 152, 152A-152H (embedded with the generator 112).

At least two longitudinal electrodes extend along each generator 112, 114 measuring about 10 cm to 15 cm. The longitudinal electrodes are embedded within the inner surface of each generator 112, 114. For example, the medial generator 112 has the longitudinal electrode 162 configured with the electrically conductive electrodes 152, 152A-152H for sensing electrical activity from several areas of the heart and for low voltage pacing of cardiac chambers nearby. The medial generator 112 also has a second high-voltage electrode 164 embedded within the inner aspect of the generator 112 that provides sensing of cardiac electrical activity, as well as for providing shock (high voltage) therapy when needed.

The lateral generator 114 has the longitudinal electrode 158 formed with the electrodes 150, 150A-150J for sensing electrical activity from several areas of the heart and for a low voltage pacing of cardiac chambers nearby. The second longitudinal electrode 160 in the lateral generator 114 is a high-voltage electrode that provides sensing of the cardiac electrical activity, as well as for providing a shock (high voltage) therapy when needed.

The double-action electrodes in the present system 100 may also include piezoelectric crystal sensors 154, 154A-154G (embedded with the generator 112) and 156, 156A-156F (embedded with the generator 114) disposed in a spaced apart relationship along the length of the generators 112, 114, respectively, at predetermined positions on the inner aspect of the generators, facing the heart.

As shown in FIGS. 2A-3, the piezoelectric crystals operate as echocardiographic sensors (154, 154A-154G, 156,

156A-156F), and Doppler sensors (166, 166A-166G) which are embedded along the inner surface of the generators 112 and 114, respectively.

High energy ultrasound transducers 180, 182 are located near each end of the system 100 to provide a noninvasive pacing to the base and the apex of the heart without the need for implanted piezoelectric crystals in the heart chambers.

In the subject system 100, the electrically conductive electrodes 150, 150A-150J, and 152, 152A-152H operate to sense the electrical activity of the heart, as well as to deliver electrical stimulation pulses (signals) passing to and from the intercostal space 104 of the patient's chest 106 to a tissue of interest.

The electrically conductive electrodes 150, 150A-150J, and 152, 152A-152H may be embedded in the respective generator(s) 112, 114, or attached to the generator's shield 120, and are positioned in a facing relationship with the heart 102 within the patient's chest 106, and may be disposed in a contiguous contact with the patient's tissue of the intercostal space 104 for sensing electrical activity of the heart, as well as for low voltage pacing and high voltage shock when commanded to by the microprocessor(s) 134.

The electrodes 150, 150A-150J, and 152, 152A-152H and component parts of the system 100 may be formed from suitable biocompatible conductive compositions, such as, for example, iridium, platinum, or like compositions, which provide optimal sensing, as well as pacing and shock.

The present system 100 also uses a piezoelectric effect which is reversible so that materials or compositions may exhibit a direct piezoelectric phenomena (the internal generation of electric charge resulting from an applied mechanical force), or alternatively, a reverse piezoelectric phenomena (the internal generation of a mechanical strain resulting from an electric field applied thereto), for example, from the electrical generator(s) 112, 114 enveloped by the electrically conductive shield 120.

Piezoelectric sensing elements 154, 154A-154G and 156, 156A-156F (which may be represented herein as ultrasonic sensing electrodes, Doppler ultrasound transducers, or acoustic sensors, as well as echo electrodes), may be formed of well-known compositions that include, for example, barium titanate and lead zirconate titanate which exhibit larger displacements when subjected to induced larger electric voltages than that found in natural mono-crystalline materials.

The piezoelectric crystals 154, 154A-154G, and 156, 156A-156F are capable of sensing mechanical activity of the heart and Doppler blood flow.

The pacing energy may be of an ultrasonic nature, which may be delivered to the heart tissues directly from the internal source 184 of the ultrasonic energy embedded within the generators 112, 114 and implanted therewith in the intercostal region 104. Due to the close proximity of the generators 112, 114 to the heart from the heart base to the heart apex, the direct delivery of the pacing pulses to the heart tissues attained by the subject system 100 is provided in an efficient manner.

In the subject system 100, the electrical generators 112, 114 serve as energy sources (both electrical and ultrasonic) and, when implanted in the patient's body, are contained within a receiving space formed by the thin flexible wall of the tube-like electrically conductive shaft 120. The electrically conductive shaft 120 is implanted within a patient's body within the intercostal space and may be secured in place by an appropriate anchoring mechanism, such as, for example, surgical sutures to obtain an adequate echocardiographic and Doppler windows of the pumping heart chambers as well as electric signals.

In this manner, the present system 100 both generates and senses electrical and ultrasonic energy directed to and from the patient's heart tissue, respectively.

As shown in FIG. 3, the electrical conductive electrodes 150, 150A-150J, and 152, 152A-152H, as well as the piezoelectric sensing elements 154, 154A-154G and 156, 156A-156F are displaced one from the other by a predetermined distance along the length of the generators/shaft.

The electrical conductive electrodes 150, 150A-150J, and 152, 152A-152H, and Doppler and ultrasound transducers electrodes 154, 154A-154G, 156, 156A-156F, 166, 166A-166G, and 168, 168A-168F, respectively, are positioned alongside the shocking longitudinal electrodes 160, 164 and the sensing longitudinal electrodes 158, 162, respectively. Each electrode component is selectively spaced at distances along the inner aspect of the generators 112, 114, or the shaft 120, to obtain the appropriate traveling signals to and from the heart.

The electrical conductive electrodes 150, 150A-150J, 152, 152A-152H are configured as longitudinal leads which may be formed of electrically conductive medically inert material, such as, for example, stainless steel, silver, or metallic paint. The electrical conductive electrodes may be attached to the generators by various means, such as, for example, welding, soldering, adhered with conductive epoxy or by placement in a pre-formed channel.

The Doppler ultrasonic transducers 166, 166A-166G, and 168, 168A-168F are formed of a piezoelectrical material having metallic conducting layers formed on their inner and outer surfaces.

In a preferred embodiment of the subject system, the Doppler and ultrasonic transducers 154, 154A-154G, 156, 156A-156G, 166, 166A-166G, and 168, 168A-168F are used both for the transmission and reception of ultrasonic energy in order to meet the size constraints imposed upon the intercostal space in order to simplify the cardiac event detection process.

The electrodes 150, 150A-150J, 152, 152A-152H may be coupled wirelessly or through wires via an interconnector with the microprocessor(s) 134. The microprocessor(s) 134 processes the EKG signals (received from the electrical conductive electrodes 150, 150A-150J, and 152, 152A-152H) and the Doppler signals (received from the piezoelectric crystal sensors 154, 154A-154G, 156, 156A-156F, 166, 166A-166G, and 168, 168A-168F) to obtain various parametric information on the electrical and mechanical activity of the heart, as well as the blood flow, for making a precise diagnosis on the tissue being examined.

Interconnections between the electric sensing, pacing and shocking electrodes 150, 150A-150J, 152, 152A-152H, 160, and 164, and the microprocessor(s) 134 (and other pacing equipment) may be provided via several mechanisms. For example, longitudinal conductive pathways, or leads may be embedded in a recess in the wall of the generator's shaft 120, on the exterior or interior surface of the generator's shaft 120, or in the lumen of the generator's shaft 120. Conductive pathways may be of identical cross-sectional area, and may be fabricated as wire conductors, coaxial cable, and optical fibers. Any flexible electrically conductive materials which are biocompatible may be used for this purpose.

The system 100 is adapted to be surgically implanted within a patient's body. In certain exemplary applications, the shield 120 may be introduced percutaneously over an adaptor using the loops 190, 192 (shown in FIG. 3) on the opposite ends of the system 100. The loops 190, 192 act as a "can electrodes" located on the outermost ends of the generators 112, 114. The implantation is performed under the fluoroscopic or ultrasound guidance into the intercostal space 104 and positioned with the pacing electrodes 150, 150A-150J, and 152, 152A-152H, the shocking (and sensing) electrodes 160 and 162, and the piezoelectric crystals 154, 154A-154G, 156, 156A-156F, 166, 166A-166G, and 168, 168A-168F, and the high energy pacing ultrasonic transducers 180 and 182 facing the desired heart chambers from the heart base to the heart apex for sensing the mechanical and electrical heart activities, and for pacing and shocking of the heart, when the cardiac situation requires.

Due to its design adapted for the specific site (the intercostal space) of implantation in the patient's body, the subject system 100 advantageously provides positioning of the electrical conductive electrodes, as well as the high voltage pacing electrodes 160, 164, low voltage pacing electrodes 158, 162 (configured with the electrical conductive electrodes 150, 150A-150J, 152, 152A-152H), and the piezoelectric elements, in close proximity to the heart 102 without intervening ribs or the sternum. In accordance with one embodiment of the present invention, the wireless piezoelectric elements 154, 154A-154G, 156, 156A-156F, 166, 166A-166G, 168, 168A-168F, and high energy pacing ultrasonic transducers 180, 182 for ultrasonic sensing and pacing are uniquely suited for being implanted within the subcutaneous tissues of the intercostal space 104.

The intercostal space 104 in close proximity to the heart 102 is an ideal location for positioning of the generators 112, 114. Being located in the intercostal space 104, the generators 112, 114 would normally be free of intervening bone matter, such as the ribs or the sternum, that might otherwise interfere with ultrasonic and electrical signals.

The generators 112, 114 are fabricated as flexible and curved members, or they may be manufactured of displaceable pacing and imaging elements so as to conform (by the configurations and dimensions) to the spaces between the ribs, and thus minimize unwanted cosmetic chest asymmetry.

The system 100 may include an anchoring mechanism for securing the shield 120 in a stable position within the intercostal space 104.

As shown in FIGS. 2A-2B and 3, in one of alternative embodiments, one or both generators 112, 114 may contain a receiver 193 and a coupling antenna 194 to enable wireless recharging of the battery 195 within the generators 112, 114 from an external power source 196. For the purposes of the wireless recharging of the generator's battery 195, the external power source 196 may be provided with a transmitter unit 197 for transmitting the energy via a transmitting antenna 198 through the skin layer.

The generators 112, 114 are percutaneously implanted within the intercostal space 104 at an optimum location determined by the ultrasonic (or echocardiographic) window. The imaging elements 154, 154A-154G, 156, 156A-156F, 166, 166A-166G, and 168, 168A-168F are disposed to face the heart 102 or the tissue to be stimulated, such as the right ventricle, left ventricular body, the apex, or the atrial appendage of the heart.

The piezoelectric crystal electrodes 154, 154A-154G, 156, 156A-156F, 166, 166A-166G, and 168, 168A-168F (also referred to as echocardiographic electrodes and Doppler ultrasound transducer electrodes) may face different views of the heart 102 from the heart base to the heart apex, in order to obtain the best reception depending on the level of intercostal muscle interference with the heart's electrical or ultrasound signals.

The generators in the present system are operable to detect cardiac electrical activity without the use of intra-cardiac electrodes.

The subject system supports the present convenient and effective method of securely implanting a pacemaker lead into the intercostal space. The locations are determined by the resultant pacing induced electrical and mechanical efficiency. The electrodes are fabricated of a suitable material such as platinum, iridium, etc., that is capable of providing optimal sensing, pacing, and shock operations.

The generators in the subject system can energize the leads when powered by the batteries and can produce electrical and ultrasound stimulation. In alternative embodiments of the subject system, the generators that energize the leads are powered by a stimulator that produces electrical current via the body tissues without the need for a wire lead.

In certain other embodiments, the generators produce ultrasound energy that is transmitted directly to the cardiac conduction tissue to cause pacing without the need for secondary piezoelectric crystals embedded within the heart.

In other embodiments, the generators have curved contours and are elongated in shape in order to conform to the intercostal space (the space between the ribs of the chest overlying the heart) and permit close proximity to cardiac structures for optimal transfer of electrical, ultrasound, Doppler, infrared and magnetic signals therewith.

In certain other embodiments, the generators are operable to emulate a 12-lead electrocardiogram by detecting cardiac electrical activity from various locations of the heart as detected from the intercostal space.

In certain other embodiments, the generators are operable to induce cardiac electrical signals without the use of wires.

In certain other embodiments, the generators are operable to detect cardiac mechanical activity by way of ultrasound and blood flow by Doppler signals without the use of intra-cardiac piezoelectric crystals.

In certain other embodiments, the generators are operable to induce cardiac mechanical contraction by way of ultrasound signals without the use of wire electrodes.

In certain other embodiments, the generators are operable to receive cardiac electrical and mechanical action and synchronize the output signals to electrodes implanted in various cardiac chambers in order to provide optimal cardiac contraction and function.

FIG. 5 depicts schematically the operational principles of the subject system 100 equipped with the microprocessor(s) 134 embedded within one or both generators 112, 114, or alternatively, operating from outside of the patient's body.

As presented in FIG. 5, a power source 200 (which may be an internal power source, an internal battery 195, or an external power source 196, or an external battery), communicating wirelessly with the generators 112, 114, the microprocessor(s) 134, as well as with the dual-action electrodes in the subject system, powers the microprocessor control/therapy unit 202 of the micro-processor(s) 134 which operates based on an algorithm 204 designed for the subject system for processing the readouts 211 from the sensors (dual-action electrodes). The microprocessor control/therapy unit 202 provides a continuous monitoring of the electrical signals, and, depending on the detected cardiac situation, provides various regimes of the therapeutic response.

The microprocessor 134 receives electric signals from the sensors (electrodes) 150, 150A-150J, and 152, 152A-152H, the wall motion signals from the piezoelectric echocardiographic sensors 154, 154A-154G, and 156, 156A-156F, the blood flow signals from the Doppler sensors 166, 166A-

166G, 168, 168A-168F, and the upright body position signals obtained from the body position sensors 210.

The algorithm 204 further underlies the processing of the signals (readouts) 211 received from the sensors to determine a cardiac situation.

In accordance with the computed cardiac situation, the microprocessor control/therapy unit 202 generates a control signal 212 indicative of a therapeutic action appropriate for the detected cardiac situation.

The detected cardiac situation coded in the control signal 212 is transmitted from the microprocessor control/therapy unit 202 to the therapy module 214, which launches a therapeutic operation commanded by the control signal 212. The therapeutic operation may be in the format of a "SHOCK" operation 216, or "ANTI-TACHICARDIA PACING" operation 218, or "BRADYCARDIA PACING" operation 220, each of which delivers a required pulse (sequence of pulses) to the heart tissues from the generators 112, 114 (specifically, the low-voltage pacing electrodes 158, 162 or high-voltage pacing electrodes 160, 164), as required, under control of the therapy module 214.

A memory unit 215 is coupled to the microprocessor control/therapy module 202 to save therein the information received therefrom. The memory unit may simultaneously record therein a stream of data measured by the sensing electrodes (electro-conductive electrodes, piezoelectric crystals, ultrasonic sensors, Doppler sensors) including electrical and mechanical activity of the heart, wall motion activity, blood flow, etc., from the heart base to the heart apex.

According to the sequence of operations depicted in FIG. 5, the microprocessors 134 direct the generators 112, 114 to deliver high voltage (shock) stimulus for ventricular fibrillation by discharging the defibrillation capacitors 222 (shown in FIGS. 2B and 3) within the generators 112, 114, low voltage anti-tachycardia pacing for rapid ventricular tachycardia, or low voltage pacing for bradycardia.

However, if a life-threatening ventricular fibrillation is detected by the microprocessor control/therapy unit 202, based on the electrical signals 211 received from the sensors, but the wall motion, Doppler blood flow and upright posture are unchanged from baseline readings (thus indicating the absence of a life-threatening event), the microprocessors 134 prevent the generators 112, 114 from delivering shocks (to prevent unwanted false pulses to the heart), and continue to monitor electrical signals from the low voltage electrodes 158, 162 (150, 150A-150J, 152, 152A-152H), as well as the high voltage electrodes 160 and 164.

An alarm may be triggered to alert the patient of impending shocks to restrict activities.

If, however, the mechanical heart activity and the Doppler's blood flow readings are absent, the microprocessor control/therapy module 202 of the microprocessors 134 commands the therapy modules 214 within the generators 112, 114 to generate a pulse, also known as "burst pacing", or "shock", to be administered to the heart.

If, however, the readings of the electrodes 154, 154A-154G, 156, 156A-156F and 166, 166A-166G, 168, 168A-168F for the electrical heart activity are non-life-threatening, but the wall motion and the Doppler blood flow signals have ceased according to sensors 154, 154A-154G, 156, 156A-156F and 166, 166A 166G, 168, 168A-168F, the microprocessors 134 render a diagnosis of "pulseless electrical activity" (PEA), or "electromechanical dissociation" for further action to be taken by the health care professionals. When the microprocessor produces the diagnosis of "pulseless electrical activity" (PEA) or electromechanical disassociation, the treatment of the causes is immediately performed. These causes may include hypovolemia, hypoxia, acidosis, hyperkalemia or hypoglycemia, hypothermia, drug overdose, cardiac tamponade, or tension pneumothorax.

Responsive to the diagnosis of non-life-threatening condition produced by the microprocessor, the causes using activation of the electrodes and sensors are searched and treated. These causes may include supraventricular tachycardia, QRS and T wave double-sensing, electromagnetic interference, diaphragmatic sensing, lead fracture, insulation break, or lead dislodgement.

In the presence of the ventricular fibrillation or flutter and very rapid ventricular tachycardia, the ventricles demonstrate no motion and cease to function as a pump, and there is an absence of blood flow detected by Doppler signals. Also, the individual will not be able to maintain an upright posture due to lack of blood supply to the brain. On the other hand, if the life-threatening arrhythmia is detected by the electrodes, but a mechanical function and blood flow and upright posture are preserved, then the arrhythmia is not life threatening and the electrical signal is associated with adequate heart function and blood flow.

Alternatively, the microprocessors 134 may also trigger the embedded electrodes to deliver pacing or shocking electric impulses in the event of an ultrasonic signal corresponding to the situation when the heart stopped pumping and there is an absence of blood flow. In this situation, the receipt of the ultrasonic signal corresponds to confirming of a life threatening heart rhythm that requires immediate electrical pacing, or shock, which requires the microprocessor to trigger the embedded electrodes to deliver the pacing or shock pulses to the heart of the patient.

The microprocessor control/therapy unit 202 provides a continuous monitoring of the electrical signals, and, depending on the detected cardiac situation, provides various regimes of the therapeutic response.

Figure 6:
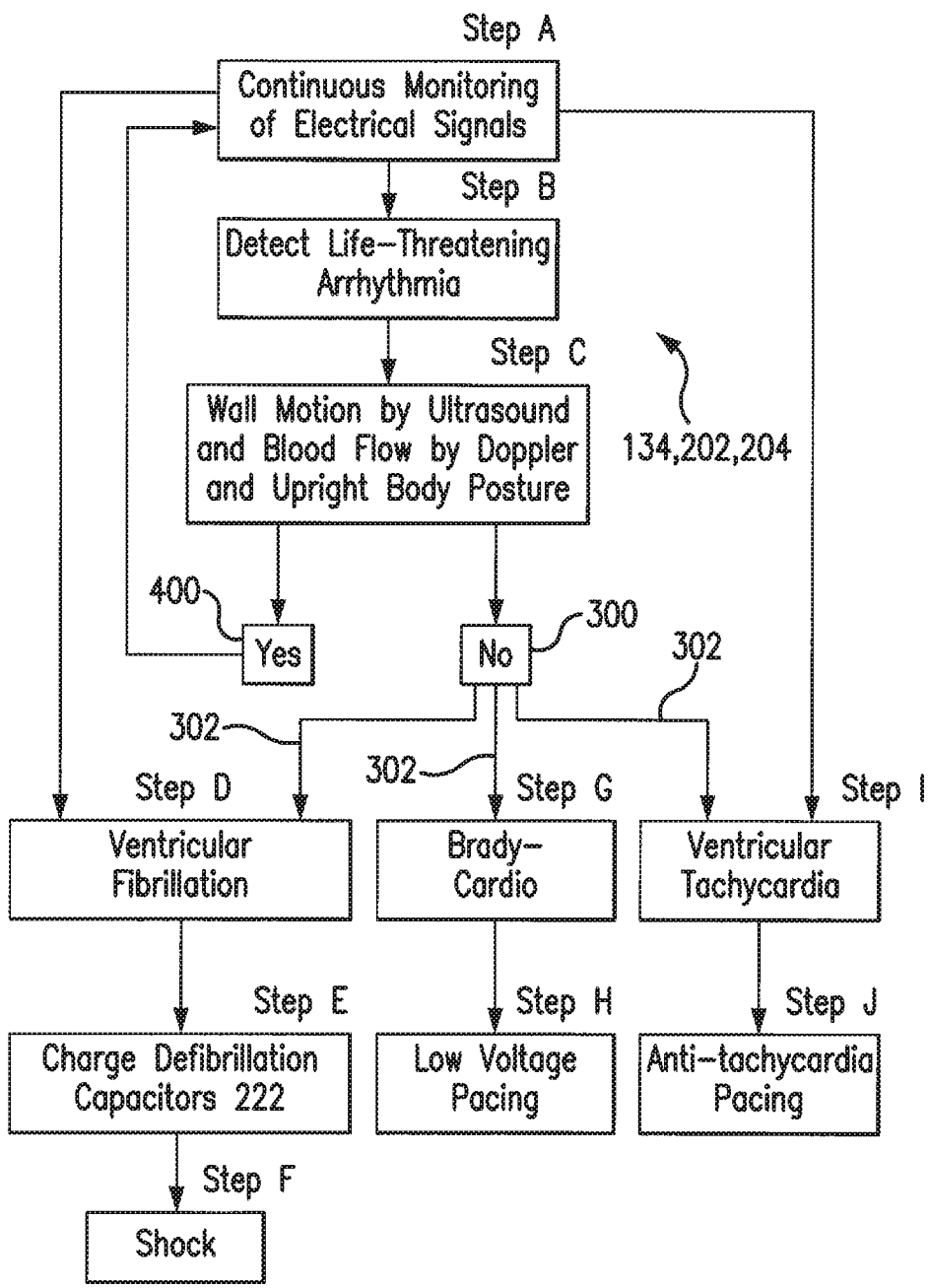
FIG. 6 is a schematic representation of the operational principles of the subject system for continuous monitoring of electrical signals corresponding to the wall motion, blood flow, and the upright body position from the sensors, producing the cardiac diagnosis, and issuing control signals for therapeutic approaches responsive to the cardiac situation, including delivery of pulses to the heart chambers if a life-threatening cardiac situation has been detected, or observation for the non-life-threatening cardiac situation.

As shown in FIGS. 5-6, in Step A, the microprocessor control/therapy unit 202 of the microprocessor(s) 134, under command of the algorithm 204, performs the continuous monitoring of electrical signals received from the sensors. If in Step B, the monitoring of the sensed signals results in the detection of a life-threatening arrhythmia, the system analyzes (in Step C) the wall motion sensing signals provided by the ultrasound sensing elements and the blood flow sensing signals generated by Doppler sensing element, as well as the upright body posture sensing signal. If the wall motion, and blood flow are absent, and the body is not in the upright position, the logic unit 300 of the microprocessor control/therapy unit 202 confirms the life-threatening cardiac condition, and generates a control signal 302 delivered to the therapy module 214 of the microprocessor 134, which, in its turn, issues a signal to launch the ventricular fibrillation (in Step D) by charging the defibrillation capacitors 222 (in Step E) and to produce a shock pulse to the heart (in Step F).

If, however, based on the sensing of the wall motion, blood flow and upright body posture in Step C, the logic unit 400 of the microprocessor control/therapy unit 202 confirms that the wall motion and blood flow present, and the patient's body maintains the upright body position (meaning that no life-threatening cardiac situation exists), the logic unit 400 commands the monitor 134 to continue monitoring of electrical signals, but not to proceed with high or low voltage pulsing.

If the logic unit 300 detects the bradycardia in Step G, the operation proceeds to Step H to generate a low voltage pacing signal transmitted to the heart.

If the ventricular tachycardia is detected in Step I as the result of continuous monitoring in Step A, and based on the signal from the logic unit 300, the procedure flows to Step J where an anti-tachycardia pacing signal is produced which is directed to the heart.

Referring to FIG. 7, presenting the routine controlled by the algorithm 204 for controlling of the LCD screen 132 and the LEDs 122A-122E, the power source 200 is connected to the microprocessor control diagnostic unit 230 which receives signals 211 from the sensing electrodes (150, 152, 154, 156, 166, 168, and 210), such as electric signals, wall motion sensing signals, Doppler blood flow sensing signals, and body position/activity sensing signals.

Depending on the reading of the sensors, the microprocessor control/diagnostic unit 230 issues LCD control signals 232 supplied to the LCD screen 132 for generating instantaneous visible representation 132A of the heart rhythm (as shown in FIG. 4) which is visible through the skin of the patient.

The microprocessor control diagnostic unit 230 also provides the LED control signal 234 to the LED units 122A-122E which are operated in a predetermined sequence, as commanded by the algorithm 204, to generate light signals of a predetermined color and sequence with a predetermined controllable pattern in the following situations:

- For the normal heart rhythm, the microprocessor control diagnostic unit 230 commands the LED units 122 to proceed to generate pulsating green light for normal A-V sequence;
- In the case of detection of the abnormal heart rate, the microprocessor control diagnostic unit 230 commands the yellow LEDs to produce a pulsating yellow signal for abnormal A-V sequence;
- In the situation when the absence of the heart rhythm is detected, the microprocessor control diagnostic unit 230 controls the red LED units to produce steady (non-pulsating) red signals.

Figure 8:
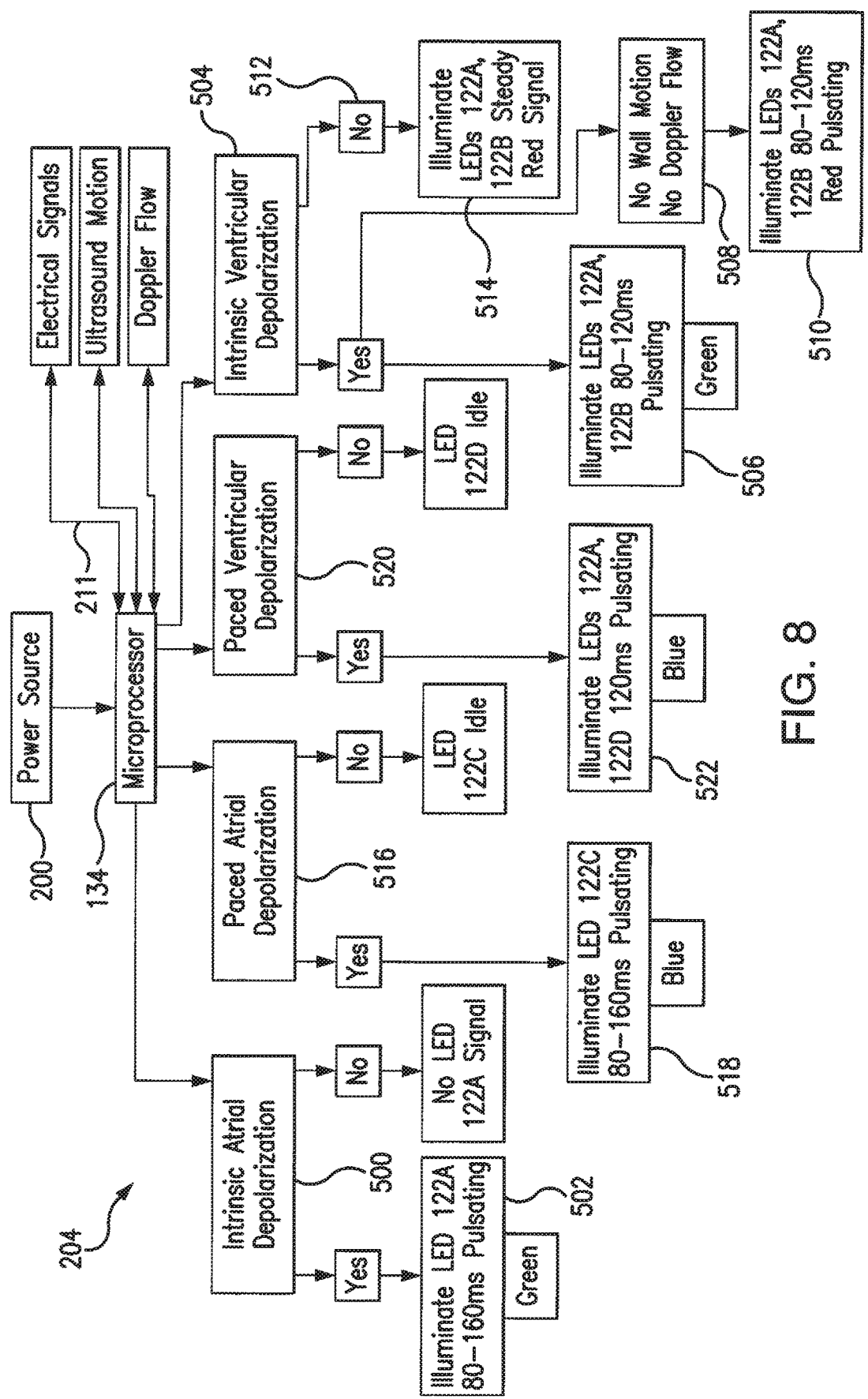
FIG. 8 is a schematic representation of the illumination routine executed by the subject microprocessor illustrating the visual representation of the heart rate, heart rhythm, pacing and shocking mode of operation, and the battery status, by displaying various light signals generated by the LEDs, as well as presented on the LCD based on the inputs from electrical electrodes, wall motion sensors, Doppler flow signals, and the body position sensor.

In one of the preferred embodiments shown in FIG. 8, an illumination algorithm (which is a part of the algorithm 204) is executed by the microprocessor(s) 134 receiving inputs 211 from the electric electrodes, ultrasound and Doppler flow signals from the atria and ventricles.

For example, the presence of intrinsic atrial depolarization detected in Step 500 by the electrodes near the atria or within the atria, may trigger (in Step 502) the instantaneous green pulsating illumination of the LED 122A for about 80-100 milliseconds at the identical rate as the intrinsic atrial depolarizations. The absence of intrinsic electrical atrial activity does not trigger a signal production by the LED 122A, indicating atrial fibrillation.

The presence of intrinsic ventricular depolarization detected (in Step 504) by electrodes near the ventricles, or within the ventricle, may trigger (in Step 506) the instantaneous pulsating illumination of the LED 122A and 122B for about 80-120 milliseconds at the identical rate as the intrinsic ventricular depolarizations.

The presence of intrinsic ventricular depolarization detected by the electrodes near or within the ventricles, but absence of wall motion and Doppler blood flow (indicating Pulseless Electrical Activity) in Step 508, may trigger in Step 510 the instantaneous pulsating red color illumination of the LEDs 122A and 122B for about 80-120 milliseconds at the identical rate as the ventricular depolarizations.

The absence of intrinsic ventricular activity detected in Step 512 triggers in Step 514 production of a steady red signal by the LEDs 122A and 122B, indicating ventricular fibrillation or asystole (cardiac arrest).

The presence of paced atrial depolarization detected in Step 516 by the electrodes near the atria, or within the atria, may trigger in Step 518 the instantaneous pulsating illumination or the LED 122C for about 80-100 milliseconds at the identical rate as the paced atrial depolarizations, pulsating blue color. The absence of paced atrial activity does not trigger a signal in the LED 122C, indicating the presence of atrial fibrillation.

The presence of paced ventricular depolarizations detected in Step 520 by the electrodes near the ventricles may trigger in Step 522 the instantaneous pulsating illumination of the LEDs 122A and 122D for about 120 milliseconds at the identical rate as the paced ventricular depolarizations, pulsating blue color. The absence of paced ventricular depolarization does not trigger a signal in the LED 122D, indicating the absence of ventricular pacing.

The multicolored LCD 132 may reflect the instantaneous display of the rate and rhythm of the depolarization and repolarization of the atria and ventricles, as shown in FIG. 4, using electrically conductive electrodes 150, 150A-150J, and 152, 152A-152H from the base to the apex of the heart. The microprocessor(s) 134 analyzes the electrocardiographic waveforms 132A for diagnosis of cardiac rhythm.

In another embodiment, the LCD display 132 and the color of the LEDs 122A-122D are determined by the input from the microprocessor(s) 134 that receive continuous data from electric, echocardiographic and Doppler signals, as well as the body position and activities.

The LCD display 132 or the LED signal (LED 122A pulsates before the LED 122B) and the pulsating green signal visible through the skin overlying the generators indicate a normal heart rhythm.

An abnormal atrioventricular sequence 132A seen on the LCD screen 132, or the signals produced by the LEDs (such as, for example, when the LED 122B lights before the LED 122A), or yellow pulsating signals, indicate an abnormal rhythm.

A pulsating red signal may indicate the presence of pulseless electrical activity (PEA) due to the presence of rhythm seen on the LCD 132, or presence of the pulsating LED red signals while the wall motion and Doppler blood flow are absent.

A steady red signal may indicate the absence of the heart rhythm, wall motion and Doppler flow (cardiac arrest).

A pulsating blue signal may indicate a low voltage pacing of the atria (LED 122C) and ventricles (LED 122D).

A steady blue signal (LED 122D) for about 3 seconds may indicate a high voltage shock.

A steady yellow signal (LED 122A) may indicate a low generator battery.

Different light patterns and sequences also may designate different heart arrhythmias.

Figure 1A:
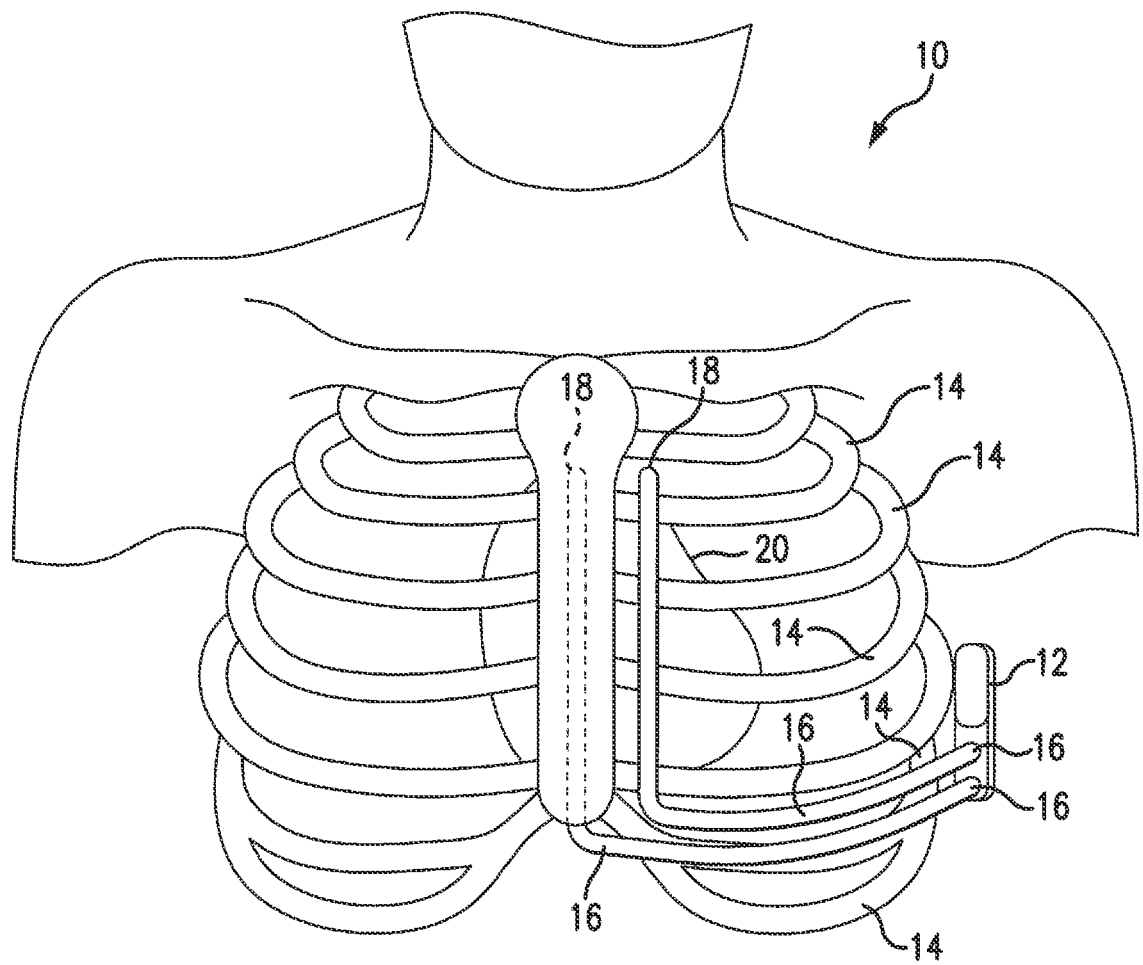
FIG. 1A is a schematic representation of a prior art subcutaneous extravascular pacemaker defibrillator system.
Figure 1B:
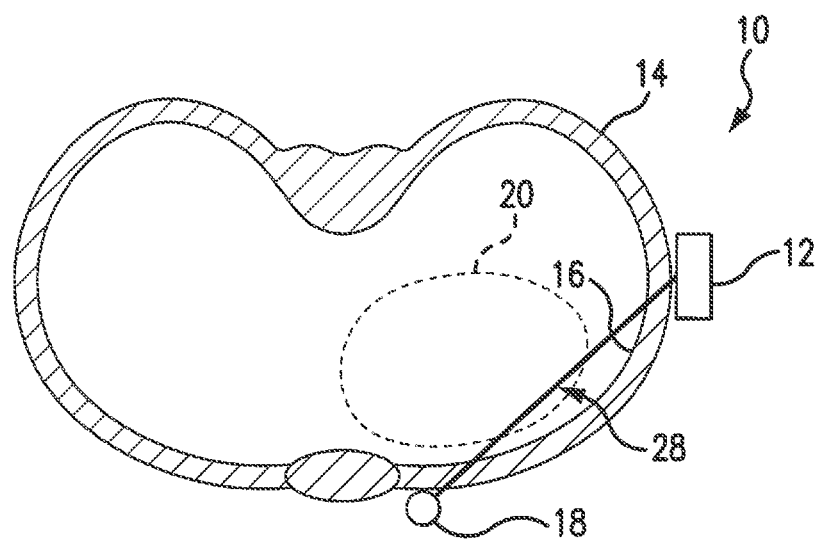
FIG. 1B is a schematic illustration of the prior art subcutaneous extravascular pacemaker defibrillator system presented in the cross-sectional view of the chest cavity of a patient showing the electric current path to shock and pace the heart.

The electrical path attained in the subject system is shorter than the electrical path 28 in the prior art system shown in FIG. 1B, and is not obstructed by anatomical structures or tissues, as opposed to conventional defibrillators.

The comparative characteristics of the subject system vs. the prior art extravascular-ICD defibrillator systems are presented in Tables 1-4.

Table 1 demonstrates the differences between the present system and characteristics of the Lee system (U.S. Patent Application Publication No. 2004/0167416).

TABLE 1

|  | Lee system | Current System |
|---|---|---|
| Monitoring of heart electricity and ultrasound | Yes | Yes |
| Shape of device: Rectangular, wide | Yes | No |
| Shape of generator: Elongated, slender | No | Yes |
| Curvilinear contour of device | No | Yes |
| Conforms to the curvature of the intercostal space | No | Yes |
| Location relative to intercostal space | Over | In |
| Fits within an intercostal space | No | Yes |
| Esthetic appearance parallel to the ribs | No | Yes |
| Closer proximity to the heart | No | Yes |
| Flexible generator | No | Yes |
| Specially designed low voltage pacing electrodes | No | Yes |
| Specially designed high voltage pacing electrodes | No | Yes |
| Likely to be uncomfortable due to rigidity | Yes | No |
| May require auxiliary leads | Yes | No |
| Provides algorithms for pacing and shocking | No | Yes |
| Equipped with generator capable of pacing | No | Yes |
| Equipped with generator capable of shocking | No | Yes |
| Rechargeable generator transcutaneously | No | Yes |
| Incorporates device position for inactivation* | No | Yes |

*Senses upright body position in order to inactivate shocking algorithm.

Table 2 compares features of the Marcovecchio system (U.S. Patent Application Publication No. 2016/0067479) with the present system.

TABLE 2

|  | Marcovecchio | Subject System |
|---|---|---|
| Lead delivery system | Yes | No |
| Leadless | No | Yes |
| Generator is Chisel-shaped | Yes | No |
| Generator is flexible | No | Yes |
| Generator shape | Rectangular | Curvilinear |
| Flexible shield member | No | Yes |
| Generator ideal for intercostal space | No | Yes |
| Generator location relative to ribs | "On ribcage" | Between ribs |
| Generator location relative to sternum | "On sternum" | Intercostal |
| Generator plane parallel to intercostal space | No | Yes |
| Path-of-travel perpendicular to intercostal space | Yes | No |
| Increased muscle injury if not perpendicular | Yes | No |
| Trauma to intercostal muscles | 100% | 0% |
| Lead goes through intercostal muscles | Yes | No |
| Lead goes through the intercostal space | Yes | No |
| System insulated from intercostal muscles | Yes | No |
| Contact of system with intercostal tissue | No | Yes |
| System functional within intercostal space | No | Yes |
| Invasiveness of system | More | Less |
| Invasion of intrathoracic cavity | Yes | No |
| Lead/electrode location within mediastinum | Yes | No |
| High risk of complications due to invasion of mediastinum | Yes | No |
| Risk of complications due to invasion of pleura | Yes | No |
| Likelihood of traumatic pneumothorax | Yes | No |
| Likelihood of mediastinitis (infection) | Yes | No |
| Likelihood of cardiac trauma due to lead proximity to a beating heart | Yes | No |
| Path-of-travel of system near vital organs and major blood vessels | Yes | No |
| Ease of diagnosis of lead/system infection | No | Yes |
| Susceptible to lead fracture | Yes | No |
| Susceptible to lead infection | Yes | No |
| Patient consents regarding benefit and risk | Unlikely | Likely |

Table 3 demonstrates features of the Sweeney system, U.S. Pat. No. 6,654,683, compared to the present system. The present system advantageously provides an extravascular, leadless and flexible curvilinear generator and is capable of attaining the high energy ultrasound pacing of the heart without intra-cardiac embedded piezoelectric crystals.

TABLE 3

|  | Sweeney | Subject System |
|---|---|---|
| Ultrasonic atrial and ventricular pacing with embedded piezoelectric crystals | Yes | Yes |
| High energy ultrasound pacing without cardiac embedded piezoelectric crystals | No | Yes |
| Leadless | No | Yes |
| Transvenous intravascular system | Yes | No |
| Extravascular subcutaneous system | No | Yes |
| Susceptible to lead fracture | Yes | No |
| Susceptible to lead infection | Yes | No |
| Flexible generator | No | Yes |
| Generator ideal for intercostal space | No | Yes |
| Likelihood of traumatic pneumothorax | Yes | No |
| Likelihood of vascular complications | Yes | No |

Table 4 demonstrates the features of extravascular implantable pacing systems presented in An, et al., U.S. Pat. No. 9,635,512, and Marshall, et al., U.S. Pat. No. 10,137, 295, vs. the subject system.

TABLE 4

|  | An and Marshall | Subject System |
|---|---|---|
| Number of generators | One | Two |
| LED equipped generator | No | Yes |
| LCD equipped generator | No | Yes |
| LED and LCD activated by body position | No | Yes |
| LED and LCD activated by body activities | No | Yes |
| Instantaneous visual normal rhythm display | No | Yes |
| Instantaneous visual abnormal rhythm display | No | Yes |
| Instantaneous visual heart rate display | No | Yes |
| Instantaneous visual low battery level display | No | Yes |
| Instantaneous visual cardiac arrest display | No | Yes |
| Instantaneous visual pacing rhythm display | No | Yes |
| Instantaneous visual shocking rhythm display | No | Yes |
| Instantaneous visual PEA* diagnosis | No | Yes |
| Ideal for Telemedicine diagnosis | No | Yes |
| Extravascular electrical stimulation | Yes | Yes |
| Defibrillation/ pacing distance | Longer | Shorter |
| Proximity to the left ventricle | Further | Closer |
| Ideal for intercostal location | No | Yes |
| Relation of generator to intercostal space | Over | Within |
| Generator overlying ribs | Yes | No |
| Electrodes overlying sternum/ribs | Yes | No |
| Flexible elongated generator design | No | Yes |
| Electrical defibrillation algorithm | Yes | Yes |
| Mechanical defibrillation algorithm | No | Yes |
| Doppler flow defibrillation algorithm | No | Yes |
| Detect electromechanical dissociation | No | Yes |
| Body position defibrillation algorithm | No | Yes |
| Ultrasound sensing of cardiac action | No | Yes |
| High energy ultrasound pacing | No | Yes |
| Ultrasound atrial pacing | No | Yes |
| Ultrasound coronary sinus pacing | No | Yes |
| Ultrasound His bundle pacing | No | Yes |

*PEA Pulseless Electrical Activity

The present description with reference made to the accompanying Drawing Figures is not to be interpreted in a limited sense. It is to be noted that the principles of the subject invention are also applicable to alternative embodiments and may be utilized without departing from the scope of the current invention, as defined in the Claims appended to this description.

What is claimed is:

1. A system for sensing and generating electrical and ultrasonic energy transmitted from and to a tissue of interest within a patient body, comprising:

an implantable flexible shield member configured in an elongated low-profile curvilinear contour conforming with and adapted to be implanted under skin within an intercostal space of a patient's body, said shield member having thin walls defining an elongated receiving space therebetween;

at least two implantable flexible generators received within said receiving space in said flexible shield member and adapted for producing and sensing electrical and ultrasonic energy associated with the tissue of interest;

a plurality of implantable double-action electrodes operatively coupled with said at least two flexible generators and adapted to be positioned in a close proximity to and in facing relation to the heart of a patient, said plurality of implantable double-action electrodes being configured to sense the electrical and mechanical activity of the heart of a patient and blood flow parameters, and provide stimulation pulses to the heart in response to a cardiac situation detected in correspondence to the sensed heart activity and the blood flow parameters; and at least one implantable liquid crystal display (LCD) and a plurality of implantable light emitting diodes (LEDs) embedded at a front surface of said at least two implantable flexible generators and implanted in the intercostal space of the patient's body, said at least one LCD and said plurality of LEDs being adapted to be positioned in a facing relationship and in close proximity to the skin overlaying said at least two implantable flexible generators, wherein said at least one implantable LCD and said plurality of implantable LEDs produce light signals corresponding to the detected cardiac situation, heart activity parameters, and to operational parameters of said at least two implantable flexible generators, wherein said light signals are transmitted through the skin overlaying said at least two implantable flexible generators and are visible external to the patient's body.

2. The system as recited in claim 1, wherein said plurality of implantable double-action electrodes includes at least one piezoelectric crystal embedded within said flexible shield member and disposed in a facing relation to the heart of the patient, said at least one piezoelectric crystal being configured to perform measurements of the heart's function by continuous or pulsed echocardiographic signals for diagnostic purposes, and to deliver high energy bursts to the heart tissue for therapeutic purposes.

3. The system as recited in claim 2, wherein said at least two implantable flexible generators embedded within said flexible shield member are configured to detect mechanical activity of the patient's heart based on the reading of said at least one piezoelectric crystal.

4. The system as recited in claim 2, wherein said at least two implantable flexible generators include an internal ultrasonic energy source operatively coupled to and implanted in the patient's body along with said at least two implantable flexible generators and said at least one piezoelectric crystal, wherein said at least one piezoelectric crystal, being powered by said internal ultrasonic energy source, produces pulsed or continuous ultrasound signals to detect the heart's mechanical function or the lack thereof.

5. The system as recited in claim 4, wherein said plurality of implantable double-action electrodes includes an echo electrode, and wherein said internal ultrasonic energy source in said at least two implantable flexible generators includes an ultrasound Doppler source positioned in proximity to and in operative coupling with said echo-electrode for pacing.

6. The system as recited in claim 5, wherein said at least two implantable flexible generators embedded within said implantable flexible shield member are configured to produce an electric shock responsive to combined acquired readings on the electrical and mechanical activity of the patient's heart when a life-threatening heart rhythm has been diagnosed.

7. The system as recited in claim 6, further including at least one microprocessor operatively coupled to said at least two implantable flexible generators, wherein said plurality of implantable double-action electrodes transmit data to said at least one microprocessor to determine presence of an electromechanical dissociation based on the electrical and mechanical signals sensed from the heart or to diagnose a life-threatening heart rhythm based on the electrical and mechanical signals sensed from the heart to avoid inappropriate shocks.

8. The system as recited in claim 4, further including an external ultrasonic generator and a transmitting antenna operatively coupled to said external ultrasonic generator, wherein said at least two implantable flexible generators embedded within said implantable flexible shield member include internal ultrasonic sources, receivers and receiving antennas operatively coupled to said receivers for wireless power transfer between said external ultrasonic generator and said internal ultrasonic energy source implanted along with said at least two implantable flexible generators in the patient's body.

9. The system as recited in claim 1, wherein said implantable flexible shield member is configured in congruence to a contour of the intercostal space.

10. The system as recited in claim 1, wherein said plurality of implantable double-action electrodes includes at least one electrically conductive electrode selected from a group consisting of high voltage shocking electrodes and low voltage pacing electrodes.

11. The system as recited in claim 10, wherein said at least two implantable flexible generators embedded within said implantable flexible shield member are configured to detect the electrical activity of the patient's heart based on the readings of said at least one electrically conductive electrode.

12. The system as recited in claim 10, wherein said at least two implantable flexible generators embedded within said implantable flexible shield member are configured to generate electrical energy directed through said high voltage shocking electrodes or said low voltage pacing electrodes to the patient's heart.

13. The system as recited in claim 1, further including an external power source and a transmitting antenna operatively coupled to said external power source, wherein said at least two implantable flexible generators embedded within said flexible shield member include receivers and receiving antennas operatively coupled to said receivers for wireless power transfer between said external power source and batteries in said at least two implantable flexible generators.

14. The system as recited in claim 1, wherein said implantable flexible shield member is formed of a biocompatible electrically-conductive composition.

15. A method for sensing energy transmitted from and generating energy transmitted to the heart of a patient, comprising:

establishing at least two implantable flexible generators contoured in congruence with the configuration of an intercostal space of a patient, operatively coupling at least one implantable instantaneous liquid crystal display (LCD) unit and a plurality of implantable light emitting diodes (LEDs) to a front surface of said at least one of said at least two implantable flexible generators, and attaching at least one parameter sensing electrode to said at least two implantable flexible generators;

implanting said at least two implantable flexible generators, said at least one implantable LCD, said plurality of implantable LEDs, and said at least one parameter sensing electrode under a skin within the intercostal space of the patient with said at least one parameter sensing electrode in proximity to and in facing positional relationship with the heart of the patient and with said at least one implantable LCD and said plurality of implantable LEDs in proximity to and in facing positional relationship with the skin overlaying said at least two implantable flexible generators;

operatively coupling at least one microprocessor to at least one of said at least two implantable flexible generators;

sensing said at least one parameter of the heart activity with said at least one parameter sensing electrode;

transmitting said sensed at least one parameter to said at least one microprocessor for processing thereat;

generating, at said at least one microprocessor, a control signal responsive to said sensed at least one parameter, and transmitting said control signal to said at least two flexible generators to produce a pacing signal if said sensed at least one parameter is indicative of a life-threatening heart condition; and displaying said sensed at least one parameter by said at least one implantable LCD and generating light signals corresponding to said control signal by said plurality of implantable LEDs to be transmitted through the skin overlaying the at least two implantable flexible generators and visible external to the patient's body.

16. The method as recited in claim 15, further comprising:
configuring said at least one microprocessor to receive input signals corresponding to the electric signal sensing, wall motion sensing, Doppler blood flow sensing and body position sensing and to determine the type of therapy required responsive to a cardiac condition, the type of therapy including at least one from a group including high voltage defibrillation shock, low voltage anti-tachycardia pacing, and low voltage pacing for bradycardia.

17. The method as recited in claim 16, further including:
configuring said at least one microprocessor with at least one control/therapy module,
coupling a memory unit to said control/therapy module of said at least one microprocessor, and
saving the information gathered by said at least one microprocessor in said memory unit.

18. The method as recited in claim 15, further including:
coupling body position sensors to said at least two generators,
sensing the upright posture of the patient with said body position sensors, and
disabling high voltage discharge routine by said microprocessor when the upright posture of the patient is detected.

19. The method as recited in claim 15, further including:
embedding a plurality of implantable double-action electrodes in said at least two implantable flexible generators, and
measuring the electric heart activity by said double-action electrodes.

20. The method of claim 19, further including:
simultaneous recording the heart electrical activity from the heart base to the heart apex by said plurality of double-action electrodes.

21. The method of claim 15, further including:
embedding a plurality of piezoelectric crystals in said at least two implantable flexible generators.

22. The method as recited in claim 15, wherein said at least one parameter sensing electrode includes a plurality of ultrasonic sensors, further providing simultaneous recording of the wall motion activity from the heart base to the heart apex from the intercostal space by said ultrasonic sensors.

23. The method as recited in claim 15, wherein said at least one parameter sensing electrode includes a plurality of Doppler sensors, further simultaneously measuring and recording blood flow from the heart base to the heart apex from the intercostal space by said Doppler sensors.

24. The method as recited in claim 15, further including:
displaying a cardiac situation corresponding to said sensed at least one parameter of the heart activity by the visual signals transmitted and seen through the skin, selected from a group including:
displaying a normal heart rhythm by said at least one instantaneous implantable LCD unit and by green color-coded signals generated by said implantable LEDs seen through the skin overlying the generators,
displaying an abnormal heart rhythm by said at least one instantaneous implantable LCD unit and by yellow color-coded signals generated by said implantable LEDs seen through the skin overlying the generators,
indicating high voltage shock of the heart at said instantaneous implantable LCD unit and by steady blue signal generated by said implantable LEDs for about 3 seconds,
indicating pulseless electrical activity (PEA) rhythm at said instantaneous implantable LCD unit and by red color-coded signals generated by said implantable LEDs seen through the skin overlying the generators, and
indicating the heart rhythm at at least one instantaneous implantable LCD unit and by signals generated by said implantable LEDs.

25. The method as recited in claim 15, further including:
embedding said at least two implantable flexible generators in an implantable flexible shield member contoured in congruence with a configuration of the intercostal space of the patient.

26. The method of claim 15, further comprising:
coupling at least one receiving antenna into said at least two implantable flexible generators,
embedding a battery in said at least two implantable flexible generators,
embedding an internal ultrasonic energy source in said at least two implantable flexible generators,
positioning a source of energy external to the patient's body, wherein said external source of energy includes a source selected from a group including an electrical power source and ultrasonic power source,
coupling a transmitting antenna to said external source of energy, and wirelessly transmitting energy from said external source of energy through said transmitting and receiving antennas to said battery and said internal ultrasonic energy source, respectively, embedded in said at least two implantable flexible generators.

* * * * *